US011180528B2

(12) United States Patent
Bishop et al.

(10) Patent No.: US 11,180,528 B2
(45) Date of Patent: Nov. 23, 2021

(54) ANTIMICROBIAL PEPTIDES AND COMPOSITIONS, METHODS, ARTICLES AND KITS RELATING THERETO

(71) Applicant: George Mason University, Fairfax, VA (US)

(72) Inventors: Barney Bishop, Annandale, VA (US); Monique Van Hoek, Centreville, VA (US); Stephanie Barksdale, Woodbridge, VA (US)

(73) Assignee: George Mason University, Fairfax, VA (US)

( * ) Notice: Subject to any disclaimer, the term of this patent is extended or adjusted under 35 U.S.C. 154(b) by 0 days.

(21) Appl. No.: 16/696,904

(22) Filed: Nov. 26, 2019

(65) Prior Publication Data

US 2020/0172570 A1    Jun. 4, 2020

Related U.S. Application Data

(60) Provisional application No. 62/772,948, filed on Nov. 29, 2018.

(51) Int. Cl.
*C07K 4/00* (2006.01)
*G01N 33/569* (2006.01)
*A61P 31/00* (2006.01)
*G01N 33/92* (2006.01)
*A61K 38/00* (2006.01)

(52) U.S. Cl.
CPC .............. *C07K 4/00* (2013.01); *A61P 31/00* (2018.01); *G01N 33/56911* (2013.01); *G01N 33/92* (2013.01); *A61K 38/00* (2013.01)

(58) Field of Classification Search
None
See application file for complete search history.

(56) References Cited

U.S. PATENT DOCUMENTS

2012/0149631 A1   6/2012   Delatour et al.
2014/0128313 A1   5/2014   Bishop et al.

OTHER PUBLICATIONS

Bishop et al. Bioprospecting the American Alligator (*Alligator mississippiensis*) Host Defense Peptidome. PLoS ONE. 2015; 10(2): e0117394. (Year: 2015).*
STN Peptide Search. CAS Registrysm: Exact and pattern searching of protein sequences. Nov. 2008. (Year: 2008).*
Barksdale et al., "Cathelicidin antimicrobial peptide from Alligator mississippiensis has antibacterial activity against multi-drug resistant Acinetobacter baumanii and Klebsiella pneumoniae", Accepted Manuscript, Jan. 10, 2017, total of 41 pages.
Barksdale et al., "Peptides from American alligator plasma are antimicrobial against multi-drug resistant bacterial pathogens including Acinetobacter baumannii", BMC Microbiology (2016) 16:189, pp. 1-14.
Bishop et al., "Bioprospecting the American Alligator (*Alligator mississippiensis*) Host Defense Peptidome", PLOS ONE | DOI:10.1371/journal.pone.0117394, Feb. 11, 2015, pp. 1-17.
Hemshekhar et al., "Functions of Cationic Host Defense Peptides in Immunity", Pharmaceuticals 2016, 9, 40, pp. 1-10.
Suvarna, "Endotoxin Detection Methods—Where are we now?", American Pharmaceutical Review | Endotoxin Supplement 2015, pp. 12-15.

\* cited by examiner

*Primary Examiner* — Soren Harward
*Assistant Examiner* — Jia-Hai Lee
(74) *Attorney, Agent, or Firm* — Potomac Law Group, PLLC

(57) ABSTRACT

Peptides are described herein, in particular peptides having antimicrobial properties, as are compositions, articles, and kits comprising such peptides, and methods for using the peptides.

17 Claims, 10 Drawing Sheets

Specification includes a Sequence Listing.

SEQUENCE LISTING

```
<160> NUMBER OF SEQ ID NOS: 11

<210> SEQ ID NO 1
<211> LENGTH: 24
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Asn or absent
<220> FEATURE:
<221> NAME/KEY: MISC_FEATURE
<222> LOCATION: (2)..(2)
<223> OTHER INFORMATION: Pro or absent
<220> FEATURE:
<221> NAME/KEY: MISC_FEATURE
<222> LOCATION: (3)..(3)
<223> OTHER INFORMATION: Lys or Arg
<220> FEATURE:
<221> NAME/KEY: MISC_FEATURE
<222> LOCATION: (4)..(4)
<223> OTHER INFORMATION: Thr, Phe, or Trp
<220> FEATURE:
<221> NAME/KEY: MISC_FEATURE
<222> LOCATION: (8)..(8)
<223> OTHER INFORMATION: Phe or Trp
<220> FEATURE:
<221> NAME/KEY: MISC_FEATURE
<222> LOCATION: (10)..(10)
<223> OTHER INFORMATION: Glu or Gln
<220> FEATURE:
<221> NAME/KEY: MISC_FEATURE
<222> LOCATION: (11)..(11)
```

```
<223> OTHER INFORMATION: His or Arg
<220> FEATURE:
<221> NAME/KEY: MISC_FEATURE
<222> LOCATION: (12)..(12)
<223> OTHER INFORMATION: Phe or Trp
<220> FEATURE:
<221> NAME/KEY: MISC_FEATURE
<222> LOCATION: (13)..(13)
<223> OTHER INFORMATION: Lys or Arg
<220> FEATURE:
<221> NAME/KEY: MISC_FEATURE
<222> LOCATION: (14)..(14)
<223> OTHER INFORMATION: Lys or Arg
<220> FEATURE:
<221> NAME/KEY: MISC_FEATURE
<222> LOCATION: (15)..(15)
<223> OTHER INFORMATION: Val, Phe, or Trp
<220> FEATURE:
<221> NAME/KEY: MISC_FEATURE
<222> LOCATION: (16)..(16)
<223> OTHER INFORMATION: Lys or Arg
<220> FEATURE:
<221> NAME/KEY: MISC_FEATURE
<222> LOCATION: (17)..(17)
<223> OTHER INFORMATION: Glu or Gln
<220> FEATURE:
<221> NAME/KEY: MISC_FEATURE
<222> LOCATION: (18)..(18)
<223> OTHER INFORMATION: Lys or Arg
<220> FEATURE:
<221> NAME/KEY: MISC_FEATURE
<222> LOCATION: (20)..(20)
<223> OTHER INFORMATION: Lys or Arg
<220> FEATURE:
<221> NAME/KEY: MISC_FEATURE
<222> LOCATION: (21)..(21)
<223> OTHER INFORMATION: Asp or Asn
<220> FEATURE:
<221> NAME/KEY: MISC_FEATURE
<222> LOCATION: (23)..(23)
<223> OTHER INFORMATION: Phe or Trp

<400> SEQUENCE: 1

Xaa Xaa Xaa Xaa Arg Asn Trp Xaa Ser Xaa Xaa Xaa Xaa Xaa Xaa
1               5                   10                  15

Xaa Xaa Leu Xaa Xaa Thr Xaa Ala
            20

<210> SEQ ID NO 2
<211> LENGTH: 22
<212> TYPE: PRT
<213> ORGANISM: Artificial Sequence
<220> FEATURE:
<223> OTHER INFORMATION: Peptide

<400> SEQUENCE: 2

Lys Phe Arg Asn Trp Phe Ser Glu His Phe Lys Lys Phe Lys Glu Lys
1               5                   10                  15

Leu Lys Asp Thr Phe Ala
            20

<210> SEQ ID NO 3
<211> LENGTH: 22
<212> TYPE: PRT
<213> ORGANISM: Artificial Sequence
<220> FEATURE:
<223> OTHER INFORMATION: Peptide

<400> SEQUENCE: 3

Lys Thr Arg Asn Trp Phe Ser Gln His Phe Lys Val Lys Gln Lys
1               5                   10                  15
```

```
Leu Lys Asn Thr Phe Ala
         20

<210> SEQ ID NO 4
<211> LENGTH: 22
<212> TYPE: PRT
<213> ORGANISM: Artificial Sequence
<220> FEATURE:
<223> OTHER INFORMATION: Peptide

<400> SEQUENCE: 4

Lys Phe Arg Asn Trp Phe Ser Gln His Phe Lys Lys Phe Lys Gln Lys
1               5                   10                  15

Leu Lys Asn Thr Phe Ala
         20

<210> SEQ ID NO 5
<211> LENGTH: 24
<212> TYPE: PRT
<213> ORGANISM: Artificial Sequence
<220> FEATURE:
<223> OTHER INFORMATION: Peptide

<400> SEQUENCE: 5

Asn Pro Lys Thr Arg Asn Trp Phe Ser Glu His Phe Lys Lys Val Lys
1               5                   10                  15

Glu Lys Leu Lys Asp Thr Phe Ala
         20

<210> SEQ ID NO 6
<211> LENGTH: 22
<212> TYPE: PRT
<213> ORGANISM: Artificial Sequence
<220> FEATURE:
<223> OTHER INFORMATION: Peptide

<400> SEQUENCE: 6

Lys Phe Arg Asn Trp Phe Ser Gln His Trp Lys Lys Trp Lys Gln Lys
1               5                   10                  15

Leu Lys Asn Thr Trp Ala
         20

<210> SEQ ID NO 7
<211> LENGTH: 22
<212> TYPE: PRT
<213> ORGANISM: Artificial Sequence
<220> FEATURE:
<223> OTHER INFORMATION: Peptide

<400> SEQUENCE: 7

Lys Phe Arg Asn Trp Phe Ser Gln His Trp Arg Arg Trp Arg Gln Arg
1               5                   10                  15

Leu Arg Asn Thr Trp Ala
         20

<210> SEQ ID NO 8
<211> LENGTH: 22
<212> TYPE: PRT
<213> ORGANISM: Artificial Sequence
<220> FEATURE:
<223> OTHER INFORMATION: Peptide

<400> SEQUENCE: 8

Arg Trp Arg Asn Trp Trp Ser Gln Arg Trp Arg Arg Trp Arg Gln Arg
1               5                   10                  15
```

```
Leu Arg Asn Thr Trp Ala
            20

<210> SEQ ID NO 9
<211> LENGTH: 22
<212> TYPE: PRT
<213> ORGANISM: Alligator mississippiensis

<400> SEQUENCE: 9

Lys Thr Arg Asn Trp Phe Ser Glu His Phe Lys Lys Val Lys Glu Lys
1               5                   10                  15

Leu Lys Asp Thr Phe Ala
            20

<210> SEQ ID NO 10
<211> LENGTH: 25
<212> TYPE: PRT
<213> ORGANISM: Alligator mississippiensis

<400> SEQUENCE: 10

Phe Ser Thr Lys Thr Arg Asn Trp Phe Ser Glu His Phe Lys Lys Val
1               5                   10                  15

Lys Glu Lys Leu Lys Asp Thr Phe Ala
            20                  25

<210> SEQ ID NO 11
<211> LENGTH: 37
<212> TYPE: PRT
<213> ORGANISM: Homo sapiens

<400> SEQUENCE: 11

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35
```

ANTIMICROBIAL PEPTIDES AND COMPOSITIONS, METHODS, ARTICLES AND KITS RELATING THERETO

CROSS-REFERENCE TO RELATED APPLICATION

This non-provisional application claims the benefit under 35 U.S.C. § 119(e) to U.S. Provisional Application No. 62/772,948, filed on Nov. 29, 2018, which is hereby expressly incorporated by reference into the present application.

GOVERNMENT INTERESTS

This invention was made with government support under Grant No. HDTRA1-12-C-0039 awarded by the Defense Threat Reduction Agency. The government has certain rights in the invention.

REFERENCE TO SEQUENCE LISTING

The Sequence Listing concurrently submitted herewith as a text file named "7074_0101PUS1_Sequence_Listing.txt," created on Nov. 20, 2019, and having a size of 4,870 bytes is herein incorporated by reference pursuant to 37 C.F.R. § 1.52(e)(5).

FIELD OF THE INVENTION

The present invention relates to peptides comprising antimicrobial properties, to compositions, kits, and articles of manufacture comprising such peptides, as well as to methods for using the peptides.

BACKGROUND

Many currently available antimicrobial agents are not effective in the treatment of pathogens including biodefense and single- or multi-drug resistant pathogens. Therefore, the search for new therapeutics with antimicrobial properties is considered a pressing need.

For example, *Francisella tularensis* is a Gram-negative bacterium that is the causative agent of tularemia. The virulent species (*F. tularensis tularensis*) can cause disease in humans with inhalation of as few as 10 organisms. In addition, this organism is easily aerosolized and has historically been developed as a bioweapon. Because of this, the United States government has classified *F. tularensis* as a Tier 1 Select Agent. *F. tularensis* is sporadically found in the United States; the CDC reports that there was an average of 215 cases per year between 2012 and 2016, and there are localized outbreaks currently occurring in Colorado and in the mid-west. The less virulent Type B strain is more commonly found to infect humans in Europe; an average of 685 cases per year were reported to the European Centre for Disease Prevention and Control from 2010 to 2014. *F. tularensis* infections (tularemia) are normally treated with fluoroquinolones and aminoglycosides but are inherently resistant to some antibiotics such as beta-lactams and polymyxins. In addition, drug resistance to conventional antibiotic treatments may be emerging in this species.

There is a need for new and effective antimicrobial agents as well as therapeutic, prophylactic, and/or diagnostic methods and strategies that target microbial organisms.

SUMMARY OF THE INVENTION

In one aspect, the present invention provides a peptide comprising:
(a) the amino acid sequence set forth in Formula (I) (SEQ ID NO:1):

$X_{aa1}$ $X_{aa2}$ $X_{aa3}$ $X_{aa4}$ Arg Asn Trp $X_{aa8}$ Ser $X_{aa10}$ $X_{aa11}$ $X_{aa12}$ $X_{aa13}$ $X_{aa14}$ $X_{aa15}$ $X_{aa16}$ $X_{aa17}$ $X_{aa18}$ Leu $X_{aa20}$ $X_{aa21}$ Thr $X_{aa23}$ Ala wherein independently of each other:
$X_{aa1}$ is Asn or absent;
$X_{aa2}$ is Pro or absent;
$X_{aa3}$ is Lys or Arg;
$X_{aa4}$ is Thr, Phe, or Trp;
$X_{aa8}$ is Phe or Trp;
$X_{aa10}$ is Glu or Gln;
$X_{aa11}$ is His or Arg;
$X_{aa12}$ is Phe or Trp;
$X_{aa13}$ is Lys or Arg;
$X_{aa14}$ is Lys or Arg;
$X_{aa15}$ is Val, Phe, or Trp;
$X_{aa16}$ is Lys or Arg;
$X_{aa17}$ is Glu or Gln;
$X_{aa18}$ is Lys or Arg;
$X_{aa20}$ is Lys or Arg;
$X_{aa21}$ is Asp or Asn; and
$X_{aa23}$ is Phe or Trp; or
(b) the amino acid sequence set forth in Formula (I) (SEQ ID NO:1) with one substitution, insertion, addition, or deletion;
with the proviso that the amino acid sequence is not native Apo6 $APOC1_{67-88}$ sequence set forth in SEQ ID NO:9.

In another aspect, the present invention provides a polynucleotide encoding the peptide of Formula (I) (SEQ ID NO:1).

In other aspects, the present invention provides a composition comprising the peptide of Formula (I) (SEQ ID NO:1) or the polynucleotide encoding the peptide of Formula (I) (SEQ ID NO:1).

In some aspects, the present invention provides an article of manufacture comprising the peptide of Formula (I) (SEQ ID NO:1).

In one aspect, the present invention provides a kit comprising the peptide of Formula (I) (SEQ ID NO:1) or the polynucleotide encoding the peptide of Formula (I) (SEQ ID NO:1).

In another aspect, the present invention provides a method for treating infection by a microbial organism in a subject. The method comprises administering to the subject the peptide of Formula (I) (SEQ ID NO:1) or the polynucleotide encoding the peptide of Formula (I) (SEQ ID NO:1).

In other aspects, the present invention provides a method for preventing, reducing or inhibiting growth of a microbial organism or biofilm on a surface. The method comprises contacting the surface with a composition comprising the peptide of Formula (I) (SEQ ID NO:1).

In some aspects, the present invention provides a method for promoting wound healing in a subject. The method comprises administering to the subject the peptide of Formula (I) (SEQ ID NO:1) or the polynucleotide encoding the peptide of Formula (I) (SEQ ID NO:1).

In one aspect, the present invention provides a method for treating or preventing endotoxemia in a subject. The method comprises administering to the subject an amount of the peptide of Formula (I) (SEQ ID NO:1) effective to treat or prevent endotoxemia in the subject.

In another aspect, the present invention provides a method for determining lipopolysaccharide (LPS) in a sample. The method comprises contacting the sample with the peptide of Formula (I) (SEQ ID NO:1) under a condition such that the LPS binds to the peptide to form a complex; and detecting the complex.

In some aspects, the present invention provides a method for diagnosing an LPS-associated disorder in a subject. The method comprises forming a complex between LPS and the peptide of Formula (I) (SEQ ID NO:1) under a condition such that the LPS binds to the peptide to form the complex; and detecting the complex.

In other aspects, the present invention provides a method for treating a composition comprising LPS. The method comprises contacting the composition with the peptide of Formula (I) (SEQ ID NO:1) under a condition such that the LPS binds to the peptide to form a complex; and separating the complex from the composition, thereby reducing or eliminating the LPS from the composition.

BRIEF DESCRIPTION OF THE DRAWINGS

FIG. 2A shows membrane depolarization was measured using DiSC3(5) in 10 mM phosphate buffer with at least 2 replicates per experiment (black=10 µg/ml; gray=1 µg/ml). Experiment was performed 3 times. FIG. 2B shows pore formation or greater membrane perturbation was measured using ethidium bromide in 10 mM phosphate buffer with 3 replicates per experiment (black=10 µg/ml; gray=1 µg/ml). Experiment was performed 3 times. Results were analyzed using a 1 way ANOVA with Dunnet's multiple comparisons. Error bars indicate experimental variation. ( $p<0.01$; ** $p<0.0001$).

FIG. 4A shows hemolysis assay using 2% sheep red blood cells. Peptides were reconstituted in sterile PBS. For 0% hemolysis, RBCs were exposed to PBS. For 100% hemolysis, RBCs were exposed to sterile water. Experiment was performed twice with 6 replicates per experiment. Results were analyzed using a 1 way ANOVA with Dunnett's multiple comparisons. FIG. 4B shows MTT cell proliferation assays using A549 human lung epithelial cells and FIG. 4C shows HepG2 human hepatocytes with 24 h exposure to 100 µg/ml peptide. Experiments were performed twice each with 3 replicates per experiment. Results were analyzed using a 1 way ANOVA with Dunnett's multiple comparisons. (* $p<0.05$;  $p<0.01$; ** $p<0.0001$). FIG. 4D shows toxicity in *G. mellonella* larvae was measured by injecting each worm with 10 µg of peptide (10 larvae/group). Survival was measured for 48 h.

FIG. 6A shows survival curves of mice with prophylactic treatment, FIG. 6B shows average health scores over course of study, FIG. 6C shows percent initial weight on day 4 after infection, in which results were analyzed using a 1 way ANOVA with Tukey's multiple comparisons (**** $p<0.0001$) Next, BALB/c mice were infected with 10 $LD_{50}$ of *F. tularensis* LVS and treated with peptide 3, 24, and 48 h after infection (5 mice/group). FIG. 6D shows survival curves of mice with post-infection treatment only, FIG. 6E shows average health scores of mice during survival study. FIG. 6F shows organ burden study comparing untreated (black bars) and GATR-3-treated (gray bars) organs (3 mice/group). Lungs, liver, and spleen were harvested on day 4 after infection homogenized in PBS and plated on chocolate agar. Results were analyzed using a 1-way ANOVA with Tukey's multiple comparisons. (**** $p<0.0001$).

DETAILED DESCRIPTION OF THE INVENTION

Figure 1:
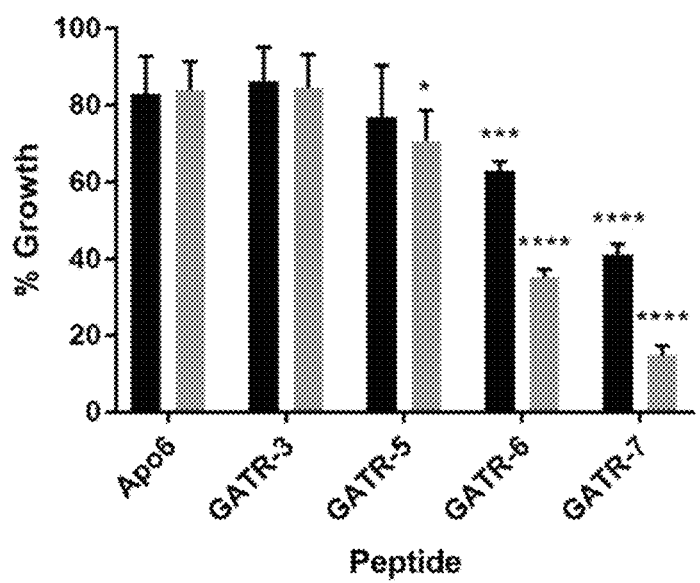
FIG. 1 is a graph showing increases in peptide hydrophobicity and charge lead to greater antimicrobial activity in broth. MIC assays were performed in Cation-adjusted Mueller Hinton Broth with 2% IsoVitaleX (black=21 µg/ml; gray=42 µg/ml) on *F. tularensis* LVS with 5 replicates per experiment. Experiment was performed twice. Results were analyzed using a 2 way ANOVA with Sidak's multiple comparison against Apo6. Error bars indicate standard deviation. (* $p<0.05$; * $p<0.001$; ** $p<0.0001$).

Disclosed herein are peptides, as well as compositions, methods, articles, and kits related to peptides, including antimicrobial peptides (AMPs), and strategies for leveraging the therapeutic and/or prophylactic potential thereof. According to various aspects and embodiments, the peptides, compositions, methods, articles, and kits provided herein can be used, among other things, for therapeutic and/or prophylactic treatment and/or prevention of an infections, wounds and/or biofilms, including infections, wounds and/or biofilms that involve a microbial organism including, but not limited to, a microbial organism that may be classified or otherwise characterized as a biodefense and/or drug- or multidrug-resistant/tolerant pathogen.

In some embodiments, the microbial organism is a bacterium, virus, fungus, or protozoa.

In one embodiment, the bacterium is a Gram-negative or Gram-positive bacterium.

In another embodiment, the bacterium is of the genus *Francisela, Acinetobacter, Pseudomonas, Klebsiella, Escherichia, Haemophilus, Proteus, Enterobacter, Serratia, Burkholderia, Stenotrophomonas, Alcaligenes, Mycobacterium, Legionella, Neisseria, Yersinia, Shigella, Vibrio*, or *Salmonella*.

In other embodiments, the bacterium is *Francisela tularensis, Acinetobacter baumannii, Pseudomonas aeruginosa, Klebsiella pneumoniae, Klebsiella oxytoca, Escherichia coli, Haemophilus influenzae, Proteus mirabilis, Enterobacter species, Serratia marcescens, Burkholderia cepacia, Stenotrophomonas maltophilia, Alcaligenes xylosoxidans, Mycobacterium tuberculosis, Neisseria gonorrhoeae, Yersinia pestis, Shigella dysenteriae, Vibrio cholera*, or *Salmonella typhi*.

In one embodiment, the bacterium is *Francisela tularensis, Francisela novicida, Francisela hispaniensis, Francisela noatunensis, Francisela philomiragia, Francisela halioticida, Francisela endociliophora, Francisela guangzhouensis*, or *Francisela piscicida.*

In another embodiment, the bacterium is *Francisela tularensis.*

In other embodiments, the bacterium is of the genus *Staphylococcus, Bacillus, Rhodococcus, Actinobacteria, Lactobacillus, Actinomyces, Clostridium*, or *Streptococcus.*

In some embodiments, the bacterium is *Staphylococcus aureus, Bacillus anthracis, Streptococcus mutans* or *Streptococcus sanguinis.*

In other embodiments, viruses include but are not limited to influenza virus, parainfluenza virus, respiratory syncytial virus, human metapneumovirus, corona virus family members, human immunodeficiency virus, herpes simplex virus, cytomegalovirus, SARS (Severe Acute Respiratory Syndrome) virus, and Epstein-Barr virus.

In some embodiments. fungi include but are not limited to *Histoplasma capsulatum, Coccidioides immitis, Blastomyces dermatitidis, Paracoccidioides brasiliensis, Candida* sp., *Aspergillus* sp., *Mucor* sp., *Cryptococcus neoformans.*

In other embodiments, protozoa include but are not limited to *Entamoeba, Acanthamoeba, Balamuthia, Leishmania, Trypanosoma, Trichomonas, Lophomonas, Cryptosporidium, Cyclospora, Toxoplasma, Plasmodium, Babesia, Encephalitozoon, Enterocytozoon* and *Balantidium.*

Subjects that can be administered or otherwise benefit from the peptides, compositions, methods, articles, and kits provided herein include vertebrates such as, without limitation, mammals. A mammal can be a human or animal including livestock and companion animals. Companion animals include but are not limited to animals kept as pets. Examples of companion animals include cats, dogs, and horses, as well as birds, such as parrots and parakeets. Livestock refers to animals reared or raised in an agricultural setting to make products such as food or fiber, or for its labor. In some embodiments, livestock are suitable for consumption by mammals, for example humans. Examples of livestock animals include mammals, such as cattle, goats, horses, pigs, sheep, including lambs, and rabbits, as well as birds, such as chickens, ducks and turkeys.

In some embodiments, the subject is a human. In another embodiment, the subject is a non-human mammal.

In other embodiments, the subject can be a human who is a medical patient (e.g., a diabetes patient, or a patient in a hospital, clinic), a member of the armed services or law enforcement, a fire fighter, or a worker in the gas, oil, or chemical industry. In one embodiment, the subject is an animal that is a veterinarian subject/patient (e.g., livestock or companion animal).

In some aspects, the sequence of a peptide of the present invention can be based on the sequence of the 22-residue Apo6 $APOC1_{67-88}$ peptide from *Alligator mississippiensis*, which said Apo6 $APOC1_{67-88}$ peptide has the sequence KTRNWFSEHFKKVKEKLKDTFA (SEQ ID NO:9).

In some embodiments, the peptides provided herein can be shorter, longer, or variant versions of the Apo6 $APOC1_{67-88}$ peptide, including peptides having one or more substitutions and/or insertions relative to the Apo6 $APOC1_{67-88}$ peptide sequence. In other embodiments, the peptides have one or more biological activities (e.g., antimicrobial).

In some embodiments, the peptides provided herein can include one or more (e.g., one, two, three, four, five or more) substitutions, insertions, deletions, and/or additions (and combinations thereof) as compared to the Apo6 $APOC1_{67-88}$ sequence set forth in SEQ ID NO:9. Amino acid substitutions can be conservative or non-conservative amino acid substitutions. Conservative amino acid substitutions can be, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitutions also include groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Non-conservative amino acid substitutions typically entail exchanging a member of one of the classes described above for a member of another class. After making an amino acid substitution, insertion, deletion, and/or addition, the activity of a peptide containing the amino acid substitution, insertion, deletion, or addition can be assessed using the assays described herein.

In other aspects, the present invention provides a peptide comprising:

(a) the amino acid sequence set forth in Formula (I) (SEQ ID NO:1):

$X_{aa1}$ $X_{aa2}$ $X_{aa3}$ $X_{aa4}$ Arg Asn Trp $X_{aa8}$ Ser $X_{aa10}$ $X_{aa11}$ $X_{aa12}$ $X_{aa13}$ $X_{aa14}$ $X_{aa15}$ $X_{aa16}$ $X_{aa17}$ $X_{aa18}$ Leu $X_{aa20}$ $X_{aa21}$ Thr $X_{aa23}$ Ala wherein independently of each other:

$X_{aa1}$ is Asn or absent;
$X_{aa2}$ is Pro or absent;
$X_{aa3}$ is Lys or Arg;
$X_{aa4}$ is Thr, Phe, or Trp;
$X_{aa8}$ is Phe or Trp;
$X_{aa10}$ is Glu or Gln;
$X_{aa11}$ is His or Arg;
$X_{aa12}$ is Phe or Trp;
$X_{aa13}$ is Lys or Arg;
$X_{aa14}$ is Lys or Arg;
$X_{aa15}$ is Val, Phe, or Trp;
$X_{aa16}$ is Lys or Arg;
$X_{aa17}$ is Glu or Gln;
$X_{aa18}$ is Lys or Arg;
$X_{aa20}$ is Lys or Arg;
$X_{aa21}$ is Asp or Asn; and
$X_{aa23}$ is Phe or Trp; or (b) the amino acid sequence set forth in Formula (I) (SEQ ID NO:1) with one or more substitutions, insertions, additions, or deletions;

with the proviso that the amino acid sequence is not native Apo6 $APOC1_{67-88}$ sequence set forth in SEQ ID NO:9.

In some embodiments, the peptide comprises the amino acid sequence set forth in SEQ ID NO:2 with one, two, three, four, or five substitutions, insertions, additions, or deletions, with the proviso that the amino acid sequence is not native Apo6 $APOC1_{67-88}$ sequence set forth in SEQ ID NO:9. In one embodiment, the peptide comprises the amino acid sequence set forth in SEQ ID NO:2.

In other embodiments, the peptide comprises the amino acid sequence set forth in SEQ ID NO:3 with one, two, three, four, or five substitutions, insertions, additions, or deletions, with the proviso that the amino acid sequence is not native Apo6 APOC1$_{67-88}$ sequence set forth in SEQ ID NO:9. In one embodiment, the peptide comprises the amino acid sequence set forth in SEQ ID NO:3.

In another embodiment, the peptide comprises the amino acid sequence set forth in SEQ ID NO:4 with one, two, three, four, or five substitutions, insertions, additions, or deletions, with the proviso that the amino acid sequence is not native Apo6 APOC1$_{67-88}$ sequence set forth in SEQ ID NO:9. In one embodiment, the peptide comprises the amino acid sequence set forth in SEQ ID NO:4.

In some embodiments, the peptide comprises the amino acid sequence set forth in SEQ ID NO:5 with one, two, three, four, or five substitutions, insertions, additions, or deletions, with the proviso that the amino acid sequence is not native Apo6 APOC1$_{67-88}$ sequence set forth in SEQ ID NO:9. In one embodiment, the peptide comprises the amino acid sequence set forth in SEQ ID NO:5.

In other embodiments, the peptide comprises the amino acid sequence set forth in SEQ ID NO:6 with one, two, three, four, or five substitutions, insertions, additions, or deletions, with the proviso that the amino acid sequence is not native Apo6 APOC1$_{67-88}$ sequence set forth in SEQ ID NO:9. In one embodiment, the peptide comprises the amino acid sequence set forth in SEQ ID NO:6.

In another embodiment, the peptide comprises the amino acid sequence set forth in SEQ ID NO:7 with one, two, three, four, or five substitutions, insertions, additions, or deletions, with the proviso that the amino acid sequence is not native Apo6 APOC1$_{67-88}$ sequence set forth in SEQ ID NO:9. In one embodiment, the peptide comprises the amino acid sequence set forth in SEQ ID NO:7.

In some embodiments, the peptide comprises the amino acid sequence set forth in SEQ ID NO:8 with one, two, three, four, or five substitutions, insertions, additions, or deletions, with the proviso that the amino acid sequence is not native Apo6 APOC1$_{67-88}$ sequence set forth in SEQ ID NO:9. In one embodiment, the peptide comprises the amino acid sequence set forth in SEQ ID NO:8.

In other embodiments, the peptides provided herein have a length of about 10 amino acids to about 50 amino acids. For example, in some embodiments, a peptide can have a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. In other embodiments, a peptide can have a length of, without limitation, about 10 to about 15 amino acids, about 15 to about 20 amino acids, about 20 to about 25 amino acids, about 25 to about 30 amino acids, about 30 to about 35 amino acids, about 35 to about 40 amino acids, about 40 to about 45 amino acids, about 45 to about 50 amino acids, about 10 to about 20 amino acids, about 20 to about 30 amino acids, about 30 to about 40 amino acids, or about 40 to about 50 amino acids.

In one embodiment, the amino acid sequence of the peptide has a length of 20 to 24 amino acids. In another embodiment, the amino acid sequence of the peptide has a length of 20 amino acids. In some embodiments, the amino acid sequence of the peptide has a length of 21 amino acids. In one embodiment, the amino acid sequence of the peptide has a length of 23 amino acids. In still other embodiments, the amino acid sequence of the peptide has a length of 24 amino acids.

In other embodiments, a peptide as provided herein has a C-terminus that is amidated.

The term "amino acid" as used herein refers to natural amino acids, unnatural amino acids, and amino acid analogs, all in their various stereoisomers (e.g., D and L stereoisomers or other allostereomers if their structures so allow). Natural (or "naturally-occurring") amino acids include the 20 "standard" amino acids that are encoded by the codons of the universal genetic code (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), as well as other "non-standard" amino acids that occur naturally but are not encoded by the codons of the universal genetic code (e.g., hydroxyproline, selenomethionine, and norleucine). Amino acids that are non-standard and/or non-naturally occurring include, without limitation, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, and pipecolic acid.

An "analog" is a chemical compound that is structurally similar to another but differs slightly in composition (as in the replacement of one atom by an atom of a different element or in the presence of a particular functional group). An "amino acid analog" therefore is structurally similar to a naturally occurring amino acid molecule as is typically found in native peptides but differs in composition such that either the C-terminal carboxy group, the N-terminal amino group, or the side-chain functional group has been chemically modified or replaced with another functional group. Amino acid analogs include natural and unnatural amino acids that are chemically blocked, reversibly or irreversibly, or modified on their N-terminal amino group or their side-chain groups, and include, for example, methionine sulfoxide, methionine sulfone, S-(carboxymethyl)-cysteine, S-(carboxymethyl)-cysteine sulfoxide and S-(carboxymethyl)-cysteine sulfone. Amino acid analogs may be naturally occurring or can be synthetically prepared. Non-limiting examples of amino acid analogs include 5-Hydroxytrpophan (5-HTP), aspartic acid-(beta-methyl ester), an analog of aspartic acid; N-ethylglycine, an analog of glycine; and alanine carboxamide, an analog of alanine. Other examples of amino acids and amino acids analogs are listed in Gross and Meienhofer, The Peptides: Analysis, Synthesis, Biology, Academic Press, Inc., New York (1983).

The stereochemistry of a peptide can be described in terms of the topochemical arrangement of the side chains of the amino acid residues about the peptide backbone, which is defined by the peptide bonds between the amino acid residues and the I-carbon atoms of the bonded residues. In addition, peptide backbones have distinct termini and thus direction. The majority of naturally occurring amino acids are L-amino acids (including the 20 standard amino acids as well as a number of other naturally-occurring, non-standard amino acids), and naturally occurring, ribosomally-produced peptides are largely comprised of L-amino acids. D-amino acids are the enantiomers of L-amino acids. Assembling peptides out of D-amino acids, which are not recognized by proteases, can enable evasion from digestion and remain intact until reaching membranes (Wade et aL, Proc Natl Acad Sci USA 87(12):4761-4765, 1990).

The peptides provided herein can be made up of L-amino acids, D-amino acids, or a combination thereof. For example, in some embodiments, a peptide can have an amino acid composition in which at least about 10% (e.g., at least about 10%, at least about 20%, at least about 25%, at least about 30%, at least about 40%, at least about 50%, at least about 60%, at least about 70%, at least about 75%, at least about 80%, at least about 85%, at least about 90%, at least about 95%) of the amino acids are D-amino acids. It is to be noted that some amino acid residues have more than one stereocenter, and the peptides provided herein can, in some embodiments, include diastereomers of these amino acids that differ from each other only in the configuration of one of their stereocenters.

In one embodiment, the peptide comprises one or more D-amino acid residues. In some embodiments, at least about 25 percent, illustratively, about 25 to 100 percent, about 50 to about 55 percent, and about 60 to about 75 percent of the amino acids in the peptide can be D-amino acids. In one embodiment, at least about 25 percent of the amino acids in the peptide can be D-amino acids. In another embodiment, 50 percent of the amino acids in the peptide can be D-amino acids. In one embodiment, at least about 75 percent of the amino acids in the peptide can be D-amino acids. In another embodiment, 100 percent of the amino acids in the peptide can be D-amino acids.

In some embodiments, peptidomimetic compounds can be used in place of the peptides provided herein. As used herein, the term "peptidomimetic" refers to compounds that are synthetic, non-peptide compounds having a three-dimensional conformation (a "peptide motif") that is substantially the same as the three-dimensional conformation of a selected peptide; a peptidomimetic compound therefore can essentially reproduce elements of amino acid structural properties and can confer the same or similar function as the selected peptide. As compared to a selected peptide, a peptidomimetic compound includes non-naturally occurring modifications, such as an altered backbone and/or non-natural amino acids. In some embodiments, for example, peptidomimetics can include beta-amino acids, peptoids, and/or N-methyl amino acids.

Peptidomimetic compounds can include amide ("peptide") or non-amide ("non-peptide") bonds in their backbone structure or can include a combination of peptide and non-peptide bonds in their backbone structure. Peptidomimetic compounds that are protease resistant or that have additional characteristics that enhance therapeutic utility, such as increased cell permeability and prolonged biological half-life, can be particularly useful. Such compounds typically have a backbone that is partially or completely non-peptide, but with side groups that are identical or similar to the side groups of the amino acid residues that occur in the peptide upon which the peptidomimetic compound is based. Several types of chemical bonds (e.g., ester, thioester, thioamide, retroamide, sulfonamide, reduced carbonyl, dimethylene and ketomethylene) can be useful substitutes for peptide bonds in the construction of peptidomimetic compounds. In some embodiments, the compounds provided herein include hybrids that contain one or more peptide portions and one or more peptidomimetic portions. Such hybrid peptides can incorporate a combination of natural amino acids and mimetic amino acids (e.g, standard amino acids and peptoids) in the same molecule.

The peptides provided herein can be obtained by any of a number of methods, including those known in the art. In some embodiments, a peptide can be obtained by extraction from a natural source (e.g., from isolated cells, tissues or bodily fluids), or can be produced by expression of a recombinant nucleic acid encoding the peptide, or by chemical synthesis (e.g., using solid phase peptide synthesis methods or a peptide synthesizer such as an ABI Peptide Synthesizer; Applied Biosystems; Foster City, Calif.). For example, standard recombinant technology using an expression vector encoding a peptide provided herein can be used. The resulting peptide then can be purified using, for example, affinity chromatographic techniques and HPLC. The extent of purification can be measured by any appropriate method, including but not limited to: column chromatography, polyacrylamide gel electrophoresis, or high-performance liquid chromatography. In some embodiments, a peptide can be designed or engineered to contain a tag sequence that allows the peptide to be purified (e.g., captured onto an affinity matrix). For example, a tag such as c-myc, hemagglutinin, polyhistidine, or FLAG™ tag (Kodak) can be used to aid peptide purification. Such tags can be inserted anywhere within the peptide, including at either the carboxyl or amino terminus. Other fusions that can be used include enzymes that aid in the detection of the peptide, such as alkaline phosphatase. In some embodiments, a peptide can be amidated at its carboxy terminus.

In some embodiments, a peptide provided herein can be isolated or purified. A "purified peptide" is a peptide that either has no naturally occurring counterpart (e.g., a peptidomimetic), or has been chemically synthesized and is thus uncontaminated by other peptides, or has been recombinantly produced and has been separated from components of the cell in which it was produced, or that has been separated or purified from other cellular components by which it is naturally accompanied (e.g, other cellular proteins, polynucleotides, or cellular components). Typically, a peptide is considered "purified" when it is at least 70%, by dry weight, free from the proteins and other molecules with which it naturally associates. A preparation of a purified peptide therefore can be, for example, at least about 80%, at least about 90%, or at least about 99%, by dry weight, the peptide. Suitable methods for purifying peptides can include, for example, affinity chromatography, immunoprecipitation, size exclusion chromatography, and ion exchange chromatography. The extent of purification can be measured by any appropriate method, including but not limited to: column chromatography, polyacrylamide gel electrophoresis, or high-performance liquid chromatography.

In one aspect, the present invention provides a polynucleotide encoding a peptide provided herein, or a nucleic acid molecule (e.g., expression vector, plasmid, etc.) comprising the polynucleotide encoding the peptide.

In other aspects, the activities of the peptides provided herein can be tested using any of a number of suitable methods, including those described in the Examples herein.

An activity of a peptide against bacteria, for example, can be tested by culturing the bacteria in a suitable liquid medium until cells reach a desired density (e.g., $OD_{600}$ of 0.8 to 1.1), and then diluting the cells to a suitable concentration in buffer containing varying concentrations of one or more selected peptides. Peptide concentrations used in the assays can range from 0 µg/ml to about 100 µg/ml with intermediate concentrations (e.g., about 0.01 µg/ml, about 0.05 µg/ml, about 0.1 µg/ml, about 0.5 µg/ml, about 1 µg/ml, about 2.5 µg/ml, about 5 µg/ml, about 7.5 µg/ml, about 10 µg/ml, about 25 µg/ml, about 50 µg/ml, 75 µg/ml, about 0.01 µg/ml to about 0.1 µg/ml, about 0.05 µg/ml to about 0.5 µg/ml, about 0.1 to about 1 µg/ml, about 0.5 µg/ml to about 5 µg/ml, about 2.5 µg/ml to about 10 µg/ml, or any other range between about 0.01 µg/ml and about 100 µg/ml) that vary for each peptide in order to maximize the number of data points. Assay cultures can be incubated for a desired length of time (e.g., about two hours), and serial dilutions of each sample can be prepared and plated. After a suitable length of incubation, colonies can be counted to determine the effectiveness of the peptide(s).

Bacterial survival at each peptide concentration can be calculated according to the ratio of the number of colonies on the plates corresponding to the peptide concentration and the average number of colonies observed for assay cultures lacking peptide. The peptide concentration required to kill about 50% of the viable cells in the assay cultures ($EC_{50}$) can be determined by plotting percent survival as a function of the log of peptide concentration (log µg/ml) and fitting the data to Equation (1) using, for example, GraphPad Prism (GraphPad Software, Inc., San Diego, Calif.), which describes a sigmoidal dose-response.

$$S = S_B + ((S_T - S_B)/(1 + 10^{(LogEC50-X)H})) \quad (1)$$

In Equation (1), S is percent survival, $S_T$ and $S_B$ represent the upper and lower survival boundaries, X is the log of the peptide concentration, and H is the Hill slope of the transition region. Another form for Equation (1) is:

$$Y = Bottom + ((Top - Bottom)/(1 + 10^{[(logEC50-X)*Hill\ Slope]})) \quad (1)$$

where Y corresponds to bacterial survival (in percentage) at a given peptide concentration (µg/ml), with X being the logarithm of that concentration. In the equation, "Top" and "Bottom" refer to the upper and lower boundaries and were constrained to values <100% and >0%, respectively.

The effect of a peptide on biofilm production can be assessed by, for example, incubating a biofilm-forming bacteria or other microbe with varying concentrations of one or more peptides for a certain length of time (e.g., 24 hours at 37° C.). Optical density of the cultures (e.g., at $OD_{600}$ nm) can be measured to assess microbial growth, and cultures then can be stained with crystal violet to assess biofilm production. See, e.g., Durham-Colleran et al., *Microb Ecol* 59(3):457-465, 2010.

An endotoxin neutralizing activity of a peptide can be assessed by, for example, the ability of the peptide to inhibit *E. coli* LPS in a rabbit pyrogenicity test or to increase the lethal dose 50 ($LD_{50}$) of *E. coli* LPS in mouse (e.g., CD1 mouse).

In another aspect, the present invention provides a composition comprising a peptide, or a polynucleotide encoding the peptide, provided herein.

For example, peptides as provided herein can be formulated in compositions by admixture with one or more pharmaceutically acceptable, non-toxic excipients or carriers. Such compositions can be used to treat or prevent microbial infection, for example. In some embodiments, a composition can include one particular peptide, while in other embodiments a composition can include two or more different peptides (e.g., peptides having different sequences or different amounts of D- and L-amino acids). In some embodiments, the compositions provided herein can contain one or more peptides at a concentration of about 0.001 µg/ml to about 100 µg/ml (e.g., about 0.001 µg/ml to about 0.01 µg/ml, about 0.005 µg/ml to about 0.05 µg/ml, about 0.01 µg/ml to about 1 µg/ml, about 0.01 µg/ml to about 10 µg/ml, about 0.05 µg/ml to about 5 µg/ml, about 0.05 µg/ml to about 25 µg/ml, about 0.1 µg/ml to about 10 µg/ml, about 0.5 µg/ml to about 50 µg/ml, about 1 µg/ml to about 100 µg/ml, or about 10 µg/ml to about 100 µg/ml.

In some embodiments, the composition further comprises an excipient. Excipients (also referred to as pharmaceutically acceptable carriers) can be liquid or solid and can be selected with the planned manner of administration in mind so as to provide for the desired bulk, consistency, and other pertinent transport and chemical properties, when combined with one or more of peptides and any other components of a given composition. Common excipients include, without limitation, sterile water, saline, polyalkylene glycols such as polyethylene glycol, oils of vegetable origin, hydrogenated naphthalenes, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). In some embodiments, biocompatible, biodegradable lactide polymer, lactide/glycolide copolymer, polyoxethylene-polyoxypropylene copolymers, or combinations thereof can be used as excipients for controlling the release of a peptide in vivo.

In other embodiments, a composition can include a peptide and one or more molecular crowding agents such as, by way of example and not limitation, FICOLL™ (e.g., FICOLL™ 70), polyethylene glycol (PEG), and dextran. FICOLL™ is a neutral, highly branched, high-mass, hydrophilic polysaccharide that dissolves readily in aqueous solutions. PEG is a polymer of ethylene oxide and is commercially available over a wide range of molecular weights from 300 g/mol to 10,000,000 g/mol. Dextran is a complex, branched polysaccharide made of glucose molecules. Without being bound by a particular mechanism, such agents may help to mimic the natural cellular environment, which may enhance the activity of the peptide. Such agents can be included in the compositions in amounts from about 5% to about 50% wt/vol (e.g., about 5%, about 10%, about 15%, about 20%, about 25%, about 30%, about 35%, about 40%, about 45%, or about 50% wt/vol, or any range there between, including about 5% to about 10%, about 10% to about 20%, about 20% to about 25%, about 25% to about 30%, about 30% to about 40%, or about 40% to about 50%).

In some embodiments, compositions can further include one or more other peptides, wherein each of the one or more other peptides has one or more biological activities (e.g., antimicrobial activity). In one embodiment, the one or more other peptides include, but are not limited to, one or more cathelicidins. Cathelicidins is known to one of ordinary skill in the art to refer to a large and diverse collection of cationic antimicrobial peptides, for example as described in U.S. Patent Publication No. 2012-0149631 A1, which is herein incorporated by reference in its entirety.

In one embodiment, compositions also can include one or more conventional antibiotics (e.g., amoxicillin, cephalexin, bacteriocin, neomycin, and/or polymyxin) and/or active ingredients from wound dressings or wound treatment compositions (e.g., NEOSPORIN®, bacitracin, and silver sulfadiazine).

Compositions can be prepared for topical (e.g., transdermal, sublingual, ophthalmic, or intranasal) administration, parenteral administration (e.g., by subcutaneous, intrathecal, intraventricular, intramuscular, or intraperitoneal injection, or by intravenous drip, in the form of liquid solutions or suspensions in aqueous physiological buffer solutions), for oral administration (e.g., in the form of tablets or capsules), or for intranasal administration (e.g., in the form of powders, nasal drops, or aerosols), depending on whether local or systemic treatment is desired and on the area to be treated. Administration can be rapid (e.g., by injection) or can occur over a period of time (e.g., by slow infusion or administration of slow release formulations). Compositions for other routes of administration also can be prepared as desired using appropriate methods. In addition, compositions can be prepared for in vitro use (e.g., for use on environmental surfaces or on medical devices).

Formulations for topical administration of peptides include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Nasal sprays also can be useful, and can be administered by, for example, a nebulizer, an inhaler, or another nasal spray device. Conventional pharmaceutical carriers, aqueous, powder or oily bases, thickeners and the like may be useful.

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Compositions and formulations for parenteral, intrathecal or intraventricular administration can include sterile aqueous solutions, which also can contain buffers, diluents and other suitable additives (e.g., penetration enhancers, carrier compounds and other pharmaceutically acceptable carriers).

In other embodiments, the composition is a pharmaceutical composition.

In some embodiments, pharmaceutical compositions can include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations can be useful for oral delivery of therapeutics due to their ease of formulation and efficacy of solubilization, absorption, and bioavailability.

Liposomes are vesicles that have a membrane formed from a lipophilic material and an aqueous interior that can contain the composition to be delivered. Liposomes can be particularly useful due to their specificity and the duration of action they offer from the standpoint of drug delivery. Liposome compositions can be formed, for example, from phosphatidylcholine, dimyristoyl phosphatidylcholine, dipalmitoyl phosphatidyl-choline, dimyristoyl phosphatidylglycerol, or dioleoyl phosphatidylethanolamine. Numerous lipophilic agents are commercially available, including LIPOFECTIN® (Invitrogen/Life Technologies, Carlsbad, Calif.) and EFFECTENE™ (Qiagen, Valencia, Calif.).

The peptides provided herein further encompass pharmaceutically acceptable salts, esters, or salts of such esters, or any other compound which, upon administration to an animal including a human, is capable of providing (directly or indirectly) the biologically active metabolite or residue thereof. Accordingly, for example, provided herein are pharmaceutically acceptable salts of peptides, prodrugs and pharmaceutically acceptable salts of such prodrugs, and other bioequivalents. The term "prodrug" indicates a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the peptides described herein (i.e., salts that retain the desired biological activity of the parent peptide without imparting undesired toxicological effects). Examples of pharmaceutically acceptable salts include, without limitation, salts formed with cations (e.g., sodium, potassium, calcium, or polyamines such as spermine), acid addition salts formed with inorganic acids (e.g., hydrochloric acid, hydrobromic acid, sulfuric acid, phosphoric acid, or nitric acid), and salts formed with organic acids (e.g., acetic acid, citric acid, oxalic acid, palmitic acid, or fumaric acid).

Compositions additionally can contain other adjunct components such as, for example, lubricants, preservatives, stabilizers, wetting agents, emulsifiers, salts for influencing osmotic pressure, buffers, colorings, flavorings, and aromatic substances. When added, however, such materials should not unduly interfere with the biological activities of the peptide components within the compositions provided herein. The formulations can be sterilized if desired.

Dosing of compositions for administration to a subject typically is dependent on the severity and responsiveness of the condition to be treated, with the course of treatment lasting, in some embodiments, from several days to several months, or in other embodiments until a cure is affected or a diminution of the condition is achieved. Persons of ordinary skill in the art routinely determine optimum dosages, dosing methodologies and repetition rates. Optimum dosages can vary depending on the relative potency of individual peptides and can generally be estimated based on $EC_{50}$ found to be effective in in vitro and in vivo animal models.

In some embodiments, dosage is about 0.01 µg to about 100 g per kg of body weight, and may be given once or more daily, biweekly, weekly, monthly, or even less often. Following successful treatment, it may be desirable to have the patient undergo maintenance therapy to prevent the recurrence of the disease state.

In some embodiments, a preliminary dosage for human infection can be inferred using guidelines put forth by the FDA (Guidance for Industry: Estimating the Maximum Safe Starting Dose in Initial Clinical Trials for Therapeutics in Adult Healthy Volunteers F.a.D. Administration, Editor. 2005 (Rockville, Md.), which is herein incorporated by reference in its entirety).

In one embodiment, dosage is at least about 0.01 mg per kg of body weight, illustratively, about 0.01 mg to about 100 mg per kg of body weight, about 0.05 mg to about 50 mg per kg of body weight, about 0.1 mg to about 10 mg per kg of body weight, about 0.4 mg to about 5 mg per kg of body weight, and may be given once or more daily, biweekly, weekly, monthly, or even less often.

In some embodiments, dosage is about 0.4 mg to about 5 mg per kg of body weight, and may be given once or more daily, biweekly, weekly, monthly, or even less often.

In other embodiments, a dose of at least about 0.01 µg is given, illustratively, about 0.01 µg to about 1 g, about 0.1 µg to about 0.1 g, about 1 µg to about 24 mg, and may be given once or more daily, biweekly, weekly, monthly, or even less often.

In other embodiments, treatments may differ if a subject is resistant or suspected of being resistant to certain antibiotics. For example, if a subject has an infection that is resistant to antibiotics, the dose may be increased, or the treatment may include two or more different peptides.

In other embodiments, one or more peptides can be admixed, encapsulated, conjugated or otherwise associated with other molecules, molecular structures, conventional antibiotics, or mixtures of compounds such as, for example, liposomes, polyethylene glycol, receptor targeted molecules, or oral, topical or other formulations, for assisting in uptake, distribution, absorption, or activity.

In still another aspect, the present invention provides an article of manufacture comprising a peptide as provided herein. In one embodiment, the article is a hygiene product (e.g., a personal hygiene product including but not limited to mouthwash and body wash). In another embodiment, the article is a wound dressing.

In some embodiments, the article is an invasive device, wherein the peptide is covalently or non-covalently attached onto a surface of the device. Covalent and non-covalent methods for attaching peptides to various surfaces are known in the art. In one embodiment, the device is a surgical tool. In another embodiment, the device is an implant. In other embodiments, the device is a catheter, a staple, a suture, an implant, or a tubing.

In still other aspects, the present invention provides a kit comprising a peptide provided herein or a polynucleotide encoding the peptide. In one embodiment, the kit further comprises instructions for using the components contained therein.

In another aspect, the present invention provides a method for treating infection by a microbial organism in a subject. The method comprises administering to the subject a peptide provided herein or a polynucleotide encoding the peptide. In one embodiment, the peptide comprises Formula (I) (SEQ ID NO:1). In another embodiment, the peptide comprises SEQ ID NO:2, 3, 4, 5, 6, 7, or 8.

In some embodiments, the infection includes but is not limited to infections of the gastrointestinal tract, respiratory system, circulatory system, lymphatic system, urinary system, muscular system, skeletal system, nervous system, and reproductive system.

In another embodiment, a method for treating an infection by a microbial organism is provided, where the method includes contacting the microbial organism with a peptide or composition as provided herein. In other embodiments, after the contacting step, growth of the microbial organism can be reduced by at least about 5 percent, illustratively, about 5 percent to 100 percent, about 10 percent to about 99.99 percent, about 20 percent to about 95 percent, about 30 percent to about 80 percent, about 40 percent to about 70 percent, and about 50 to about 60 percent when measured in an assay to measure colony formation. In some embodiments, after the contacting, growth of the microbial organism can be reduced by at least about 50 percent when measured in an assay to measure colony formation.

In other embodiments, the infection can be a polymicrobial infection.

In some embodiments, for example, a peptide or a composition comprising the peptide as described herein can be used to treat a subject having a microbial (e.g., bacterial or fungal) infection, such as in a wound that is in or on a subject (e.g., a mammal such as, without limitation, a human). Wounds can result from accidental occurrences, or can result from, for example, medical procedures.

In some embodiments, the subject can be a human who is a medical patient (e.g., a diabetes patient, or a patient in a hospital, clinic, or veterinary setting), a member of the armed services or law enforcement, a fire fighter, or a worker in the gas, oil, or chemical industry. In one embodiment, the subject is an animal suitable to be treated by a veterinarian including, but not limited to pets and livestock/farm animals.

In other aspects, the present invention provides a method for preventing, reducing or inhibiting growth of a microbial organism or biofilm on a surface. The method comprises contacting the surface with a composition comprising a peptide provided herein. In one embodiment, the peptide comprises Formula (I) (SEQ ID NO:1). In another embodiment, the peptide comprises SEQ ID NO:2, 3, 4, 5, 6, 7, or 8.

In one embodiment, the surface is an environmental surface. In another embodiment, the surface is on a prosthetic or an implant. In other embodiments, the surface is in a living organism (e.g., a human or a non-human animal). In some embodiments, the peptides and compositions described herein are used in surface coatings for medical devices (e.g., catheters, prosthetics, implants, and other indwelling devices), or in dressings to be applied to a wound on or in a patient.

Biofilms are aggregates of microorganisms in which cells adhere to each other on a surface. Without wishing to be bound by any particular theory, it is believed that the adherent cells frequently are embedded in a self-produced matrix of extracellular polymeric substance (EPS) that generally is composed of extracellular DNA, proteins, and polysaccharides. Biofilms are ubiquitous, and can form on virtually any non-shedding, living or non-living surface in a non-sterile aqueous (or very humid) environment. Biofilms can be found, for example, in natural, industrial, hospital, and veterinary settings. Biofilms can be involved in a wide variety of microbial infections in the body, including common problems such as urinary tract infections, catheter infections, ear infections, formation of dental plaque, gingivitis, coating contact lenses, and less common but more serious conditions such as endocarditis, infections in cystic fibrosis, and infections of permanent indwelling devices such as joint prostheses and heart valves. Bacterial biofilms also can impair cutaneous wound healing and reduce topical antibacterial efficiency in healing or treating infected skin wounds.

Chronic opportunistic infections in immunocompromised patients and the aging population are a major challenge for medical professionals, as traditional antibiotic therapies usually are not sufficient to eradicate the infections. One reason for their persistence seems to be the capability of the bacteria to grow within biofilms that protect them from adverse environmental factors. *Pseudomonas aeruginosa* is an example of an opportunistic pathogen and a causative agent of emerging nosocomial infections. Other examples of microbes that can form medically relevant biofilms include, without limitation, *Streptococcus mutans* and *Streptococcus sanguinis*, which are involved in formation of dental plaque, *Legionella bacteria*, and *Neisseria gonorrhoeae*, which can form biofilms on human cervical epithelial cells.

In some embodiments, after the contacting, growth of the biofilm can be reduced by at least about 5 percent, compared to a control, when measured in an assay to measure optical density. In other embodiments, after the contacting, growth of the biofilm is reduced by at least about 25 percent, compared to a control when measured in an assay to measure optical density.

In other aspects, the present invention provides a method for promoting wound healing in a subject. The method comprises administering to the subject the peptide of Formula (I) (SEQ ID NO:1) or the polynucleotide encoding the peptide of Formula (I) (SEQ ID NO:1). In another embodiment, the peptide comprises SEQ ID NO:2, 3, 4, 5, 6, 7, or 8.

In some embodiments, the peptides and compositions described herein can be used in methods for promoting healing of wounds that are not infected (or that show no evidence of infection). For example, in some embodiments, a peptide or composition comprising one or more peptides described herein can be useful for treating an uninfected wound in a subject (e.g., a vertebrate such as a human), for example such that the wound has increased numbers of keratinocytes, shrinks in size more rapidly, and/or heals more quickly than it would without administration of the peptide or composition. In some embodiments, treatment of an uninfected wound with a peptide or composition can be considered effective if the wound size is reduced by at least about 5% (e.g., at least about 10%, at least about 20%, at least about 25%, at least about 30%, at least about 40%, at least about 50%, at least about 60%, at least about 70%, at least about 75%, at least about 80%, at least about 90%, or at least about 95%) during or after treatment, as compared to a control (e.g., a time point before or earlier in the treatment).

In one aspect, the peptides and compositions also can be used in methods that include determining whether a subject having a microbial infection is resistant to one or more conventional antibiotics (e.g., methicillin), or is suspected of being resistant to one or more conventional antibiotics. If the subject is determined to be resistant to the one or more conventional antibiotics or is suspected of being resistant to the one or more conventional antibiotics, the subject can be treated with a peptide or composition provided herein. In contrast, if the subject is determined not to be resistant to the one or more conventional antibiotics or is not suspected of being resistant to the one or more conventional antibiotics, the subject can be treated with the one or more conventional antibiotics. In such methods, the subject can be monitored to determine whether the treatment is effective, and the treatment can be adjusted accordingly. For example, if the subject is treated with one or more conventional antibiotics but is subsequently determined to be resistant to the conventional antibiotic(s), the subject can be treated with a peptide or composition as provided herein. In some embodiments, the subject can be treated with one or more AMPs and conventional antibiotics contemporaneously (e.g., in cases of severe infection insufficient time to try one or the other treatments).

In another aspect, the peptides and compositions provided herein can be used in methods for improving the effectiveness of treatment for microbial infection. For example, a method can include administering to a subject an amount of a peptide or composition that is sub-anti-microbial but is effective to reduce biofilm levels or inhibit biofilm formation or administering a peptide under conditions that are sub-anti-microbial but are effective to reduce biofilm levels or inhibit biofilm formation. For example, a peptide may be less effective as an anti-microbial agent under high salt conditions (e.g., about 125 to about 150 mM salt, including about 130 mM, about 135 mM, about 140 mM, or about 145 mM salt), but can retain effectiveness as an anti-biofilm agent under such conditions. After one or more sub-anti-microbial treatments, the subject can be treated with an anti-microbial amount of the peptide or composition, with the peptide under conditions that are anti-microbial, or with one or more conventional antibiotics. The sub-anti-microbial and anti-microbial treatments can be separated by any length of time, ranging from an hour or less to several hours to a day or more (e.g., about 0.5 hour, about one hour, about two hours, about three hours, about four hours, about six hours, about 12 hours, about 1 day, or more than 1 day). Treatments can be repeated as needed or desired.

The effectiveness of a peptide or composition containing one or more peptides as described herein can be determined by assessing microbial growth or biofilm growth before, during, and/or after treatment. In some embodiments, for example, samples can be obtained from a subject before treatment, and at one or more different time points during or after treatment with a peptide or composition as provided herein, and microbial growth can be measured by counting the number of colonies that grow up from the samples after they are plated on a solid medium. Biofilm growth can be measured based on optical density (e.g., at 600 nm) and/or staining with crystal violet, for example. Treatment with a peptide or composition can be considered effective if microbial growth or biofilm formation is reduced by at least about 5% (e.g., at least about 10%, at least about 20%, at least about 25%, at least about 30%, at least about 40%, at least about 50%, at least about 60%, at least about 70%, at least about 75%, at least about 80%, at least about 90%, or at least about 95%) during or after treatment, as compared to a control (e.g., a time point before or earlier in the treatment).

Lipopolysaccharide (LPS) is a major structural component of the Gram-negative bacterial outer membrane and is believed to protect bacteria from antimicrobial compounds. LPS from *E. coli* and other Gram-negative bacteria is the endotoxin and, for example, may activate innate immunity through binding TLR4 receptors. Administration of parenteral products contaminated with pyrogens including LPS may lead to, for example, development of fever, induction of inflammatory response, shock, organ failure and death in humans or animals.

Without wishing to be bound by any particular theory, it is believed that the overall positive charge on certain antimicrobial peptides may assist them to form strong electrostatic interactions with the negatively charged LPS in the membrane of Gram-negative bacteria neutralizing the overall negative charge. The binding of such peptides with LPS of Gram-negative bacteria can have a major effect on the stability of bacterial membranes. Several cationic antimicrobial peptides including LL-37, SMAP-29, and CAP18 can bind LPS. Some antimicrobial peptides can reduce the host immune response to LPS by binding and sequestering it.

In one aspect, the present invention provides a method for treating or preventing endotoxemia in a subject. The method comprises administering to the subject an amount of the peptide of Formula (I) (SEQ ID NO:1) effective to bind to an endotoxin so as to treat or prevent endotoxemia in the subject. In another embodiment, the peptide comprises SEQ ID NO:2, 3, 4, 5, 6, 7, or 8.

In some embodiments, the endotoxemia is associated with endotoxin related shock including, but not limited to, septic shock, bacteremia-induced shock, and circulatory shock induced by endotoxin.

In other embodiments, the peptide binds to the endotoxin it encounters in the subject, thereby forming a conjugate that has reduced toxicity and pathogenicity relative to unconjugated endotoxin.

In one embodiment, the peptide binds to the endotoxin it encounters in the subject but does not cause bacterial lysis so as to prevent endotoxin-induced lethality.

In other embodiments, the peptide is covalently or non-covalently attached onto a surface of an invasive device, wherein the endotoxin contacts the peptide on the surface of the device during or following an invasive procedure carried out on the subject.

In one embodiment, the device is a surgical tool.
In another embodiment, the device is an implant.
In other embodiments, the device is a catheter, a staple, a suture, an implant, or a tubing.

In some embodiments, the endotoxin is a LPS of a Gram-negative bacterium.

In another embodiment, the bacterium is of the genus *Francisela, Acinetobacter, Pseudomonas, Klebsiella, Escherichia, Haemophilus, Proteus, Enterobacter, Serratia, Burkholderia, Stenotrophomonas, Alcaligenes, Mycobacterium, Legionella, Neisseria, Yersinia, Shigella, Vibrio,* or *Salmonella.*

In other embodiments, the bacterium is *Francisela tularensis, Acinetobacter baumannii, Pseudomonas aeruginosa, Klebsiella pneumoniae, Klebsiella oxytoca, Escherichia coli, Haemophilus influenzae, Proteus mirabilis, Enterobacter species, Serratia marcescens, Burkholderia cepacia, Stenotrophomonas maltophilia, Alcaligenes xylosoxidans, Mycobacterium tuberculosis, Neisseria gonorrhoeae, Yersinia pestis, Shigella dysenteriae, Vibrio cholera,* or *Salmonella typhi.*

In one embodiment, the bacterium is *Francisela tularensis, Francisela novicida, Francisela hispaniensis, Francisela noatunensis, Francisela philomiragia, Francisela halioticida, Francisela endociliophora, Francisela guangzhouensis,* or *Francisela piscicida.*

In another embodiment, the bacterium is *Francisela tularensis.*

In other aspects, a device coated with a peptide of Formula (I) (SEQ ID NO:1) is provided. In another embodiment, the peptide comprises SEQ ID NO:2, 3, 4, 5, 6, 7, or 8.

In one embodiment, the device is a surgical tool.

In another embodiment, the device is an implant.

In other embodiments, the device is a catheter, a staple, a suture, an implant, or a tubing.

In another aspect, the present invention provides a method for determining lipopolysaccharide (LPS) in a sample. The method comprises contacting the sample with the peptide of Formula (I) (SEQ ID NO:1) under a condition such that the LPS binds to the peptide to form a complex; and detecting the complex. In some embodiments, the peptide comprises SEQ ID NO:2, 3, 4, 5, 6, 7, or 8.

In one embodiment, the sample is a biological fluid sample obtained from the subject.

In another embodiment, the sample comprises serum, urine, blood, tissue extract or sputum.

In some embodiments, the sample comprising the LPS is transferred onto a suitable support under a condition permitting LPS in the sample to attach to the support prior to contacting the sample with the peptide.

In another embodiment, the peptide comprises a detectable label.

In some embodiments, the label comprises a fluorescent moiety, a radioactive moiety, or an enzyme.

In other aspects, the present invention provides a method for diagnosing a LPS-associated disorder in a subject. The method comprises forming a complex between LPS and the peptide of Formula (I) (SEQ ID NO:1) under a condition such that the LPS binds to the peptide to form the complex; and detecting the complex. In some embodiments, the peptide comprises SEQ ID NO:2, 3, 4, 5, 6, 7, or 8.

In some embodiments, the endotoxin is a LPS of a Gram-negative bacterium.

In another embodiment, the bacterium is of the genus *Francisela, Acinetobacter, Pseudomonas, Klebsiella, Escherichia, Haemophilus, Proteus, Enterobacter, Serratia, Burkholderia, Stenotrophomonas, Alcaligenes, Mycobacterium, Legionella, Neisseria, Yersinia, Shigella, Vibrio,* or *Salmonella.*

In other embodiments, the bacterium is *Francisela tularensis, Acinetobacter baumannii, Pseudomonas aeruginosa, Klebsiella pneumoniae, Klebsiella oxytoca, Escherichia coli, Haemophilus influenzae, Proteus mirabilis, Enterobacter species, Serratia marcescens, Burkholderia cepacia, Stenotrophomonas maltophilia, Alcaligenes xylosoxidans, Mycobacterium tuberculosis, Neisseria gonorrhoeae, Yersinia pestis, Shigella dysenteriae, Vibrio cholera,* or *Salmonella typhi.*

In one embodiment, the bacterium is *Francisela tularensis, Francisela novicida, Francisela hispaniensis, Francisela noatunensis, Francisela philomiragia, Francisela halioticida, Francisela endociliophora, Francisela guangzhouensis,* or *Francisela piscicida.*

In another embodiment, the bacterium is *Francisela tularensis.*

In one embodiment, the LPS is present in a sample obtained from the subject.

In another embodiment, the method further comprises obtaining a sample from the subject and detecting the complex in the sample.

In one embodiment, the sample is a biological fluid sample obtained from the subject.

In another embodiment, the sample comprises serum, urine, blood, tissue extract or sputum.

In some embodiments, the sample comprising the LPS is transferred onto a suitable support under a condition permitting LPS in the sample to attach to the support prior to contacting the sample with the peptide.

In another embodiment, the peptide comprises a detectable label.

In some embodiments, the label comprises a fluorescent moiety, a radioactive moiety, or an enzyme.

In other aspects, the present invention provides a method for treating a composition comprising a LPS. The method comprises contacting the composition with the peptide of Formula (I) (SEQ ID NO:1) under a condition such that the LPS binds to the peptide to form a complex; and separating the complex from the composition, thereby reducing or eliminating the LPS from the composition. In some embodiments, the peptide comprises SEQ ID NO:2, 3, 4, 5, 6, 7, or 8.

In one embodiment, the composition is for parenteral administration.

In another embodiment, the composition is for oral, intravenous, intramuscular, or subcutaneous administration.

In some embodiments, the composition is a cell culture reagent.

In other embodiments, the composition is blood, plasma, serum, or bone marrow.

In some embodiments, the endotoxin is a LPS of a Gram-negative bacterium.

In another embodiment, the bacterium is of the genus *Francisela, Acinetobacter, Pseudomonas, Klebsiella, Escherichia, Haemophilus, Proteus, Enterobacter, Serratia, Burkholderia, Stenotrophomonas, Alcaligenes, Mycobacterium, Legionella, Neisseria, Yersinia, Shigella, Vibrio,* or *Salmonella.*

In other embodiments, the bacterium is *Francisela tularensis, Acinetobacter haumannii, Pseudomonas aeruginosa, Klebsiella pneumoniae, Klebsiella oxytoca, Escherichia coli, Haemophilus influenzae, Proteus mirabilis, Enterobacter species, Serratia marcescens, Burkholderia cepacia, Stenotrophomonas maltophilia, Alcaligenes xylosoxidans, Mycobacterium tuberculosis, Neisseria gonorrhoeae, Yersinia pestis, Shigella dysenteriae, Vibrio cholera,* or *Salmonella typhi.*

In one embodiment, the bacterium is *Francisela tularensis, Francisela novicida, Francisela hispaniensis, Francisela noatunensis, Francisela philomiragia, Francisela halioticida, Francisela endociliophora, Francisela guangzhouensis,* or *Francisela piscicida.*

In another embodiment, the bacterium is *Francisela tularensis.*

The invention will be further described in the following examples, which do not limit the scope of the invention described in the claims.

EXAMPLES

Example 1

Materials and Methods

Bacterial strains. *Francisella tularensis* subsp. *holarctica* CDC Live Vaccine Strain (NR-646), *F. tularensis* subsp. *tularensis* NIH B38 (NR-50) and *F. tularensis* subsp. *tularensis* SchuS4 (NR-10492) were obtained from BEI Resources (Manassas, Va.). Bacteria were grown 48-72 h on chocolate II agar (BD 211267) at 37° C. with 5% $CO_2$. Prior to the experiments below, bacteria were scraped off the plate and resuspended to 0.5 McFarland units in phosphate buffered saline (PBS) or Buffer Q [6.12 mM sodium monohydrogen phosphate heptahydrate; 3.92 mM monosodium phosphate anhydrous; 0.3 g/L tryptic soy broth (BD211825); 1 mg/L cysteine HCl] or 10 mM phosphate buffer. A standard curve of bacteria was used to determine the CFU equivalents (0.5 McFarland units=$1\times10^7$ CFU/ml). Resuspended bacteria were then diluted to the appropriate concentration needed. All work with *F. tularensis* SchuS4 was performed in a BSL-3 laboratory.

Peptide Synthesis. Peptides were synthesized by ChinaPeptides, Inc (Shanghai, China) using Fmoc chemistry. Peptide was provided at >95% purity, which was confirmed with RP-HPLC and ESI-MS. Sequences and physico-chemical properties are shown in Table 1.

Peptide properties. Physico-chemical properties and helical wheels were calculated using Heliquest (Gautier, R., et al., Bioinformatics, 2008. 24(18): p. 2101-2).

Minimal inhibitory concentration (MIC) determination assay. MICs were determined according to CLSI guidelines for this organism (Georgi, E., et al., J Antimicrob Chemother, 2012. 67(10): p. 2429-33; Institute, C.a.L.S., Performance Standards for Antimicrobial Susceptibility Testing, in M100-S22. 2012, CLSI: Wayne, Pa., USA). Briefly, *Francisella* bacteria were grown on chocolate II agar (BD 221169) for 48-72 h prior to experiments. Minimal inhibitory concentration experiments were performed in Cation-adjusted Mueller Hinton Broth (BD 212322, CAMHB) with 2% IsovitaleX (BD 211875) using polypropylene plates. Approximately $3*10^4$ were added to each well, as determined using a McFarland standard curve for *Francisella*. Results were analyzed at 21 and 42 µg/ml using a two-way ANOVA with Sidak's multiple comparisons.

Antimicrobial assays. The antimicrobial activity of antimicrobial peptides against *F. tularensis* was determined as described previously (Han, S., B. M. Bishop, and M. L. van Hoek, Biochem Biophys Res Commun, 2008. 371(4): p. 670-4; Amer, L. S., B. M. Bishop, and M. L. van Hoek, Biochem Biophys Res Commun, 2010. 396(2): p. 246-51; Kaushal. A., et al., Dev Comp Immunol, 2016. 63: p. 171-180). Briefly, in a 96 well plate, $1\times10^5$ CFU per well were incubated with various peptide concentrations in Buffer Q for 3 h at 37° C. (total volume 100 µl). After the incubation, well contents were serially diluted, and 5 µl of each dilution was spotted onto chocolate agar and allowed to dry. Agar plates were incubated overnight (18 hr) at 37° C. and the colonies were counted. The concentration of peptide required to kill 50% of microbial population ($EC_{50}$) was analyzed by analyzing the percentage of surviving colonies after the overnight incubation as a function of log of peptide concentration. The data was analyzed through GraphPad Prism 6 (GraphPad Software Inc. San Diego, Calif., USA). The antimicrobial activity of the GATR peptides was compared to the activity of LL-37, a human cathelicidin with

TABLE 1

Sequences and physico-chemical properties of peptides

| Name‡ | Sequence/SEQ ID NO/Boman Index | Molecular Weight | Charge | Hydrophobic Moment (µH) | Hydrophobicity (H) |
|---|---|---|---|---|---|
| Apo5 APOC1$_{64-88}$ | FSTKTRNWFSEHFKKVKEKLKDTFA/SEQ 10 | 3103.57 | +4 | 0.436 | 0.155 |
| Apo6 APOC1$_{67-88}$ | KTRNWFSEHFKKVKEKLKDTFA/SEQ 9 | 2768.21 | +4 | 0.484 | 0.085 |
| GATR-1 | KFRNWFSEHFKKFKEKLKDTFA/SEQ 2 | 2862.31 | +4 | 0.564 | 0.180 |
| GATR-2 | KTRNWFSQHFKKVKQKLKNTFA/SEQ 3 | 2765.34 | +7 | 0.441 | 0.130 |
| GATR-3 | KFRNWFSQHFKKFKQKLKNTFA/SEQ 4/2.69 | 2859.35 | +7 | 0.523 | 0.226 |
| GATR-4 | NPKTRNWFSEHFKKVKEKLKDTFA/SEQ 5 | 2973.41 | +4 | 0.405 | 0.082 |
| GATR-5 | KFRNWFSQHWKKWKQKLKNTWA/SEQ 6/2.78 | 2976.46 | +7 | 0.566 | 0.289 |
| GATR-6 | KFRNWFSQHWRRWRQRLRNTWA/SEQ 7/4.91 | 3116.55 | +7 | 0.568 | 0.284 |
| GATR-7 | RWRNWWSQRWRRWRQRLRNTWA/SEQ 8/5.86 | 3241.69 | +8 | 0.578 | 0.273 |
| LL-37 | LLGDFFRKSKEKIGKEFKRIVQRIKDFLRNLVPRTES/SEQ 11 | 4493.33 | +6 | 0.521 | 0.201 |

‡GATR-1 through -7 are herein collectively also referred to as "GATR peptides."

known antibacterial activity against *Francisella*. The confidence intervals along with the $EC_{50}$ values for each peptide are reported in Table 2. Samples were run in triplicate on three separate occasions.

Membrane depolarization assay. Membrane potential was measured using a fluorescent assay utilizing $DiSC_3(5)$ dye as previously described with some modification. *F. tularensis* LVS was grown on chocolate II agar (48 h, 37° C., 5% $CO_2$), and the colonies were suspended in 10 mM phosphate buffer to 0.5 McFarland standard. 100 μL of this suspension was added to wells of a black polypropylene 96 well plate. The plate was incubated in a Tecan Infinite F200 fluorimeter. A change in the fluorescence was monitored until equilibrium is reached, evidenced by quenching of the fluorescent signal, indicating maximum uptake of the dye by the membrane. The experimental wells were then treated with 100 μl of various concentrations of peptide diluted in 10 mM phosphate buffer. The plate was returned to the spectrofluorometer and readings were taken every min for 15 min (excitation=620 nm; emission=670 nm). Peak RFU at each concentration was used in FIG. 2A. Samples were run in triplicate on two separate occasions. Bacteria without peptide treatment was used as a negative control, and LL-37 was used as positive control. Depolarization results were analyzed using a one-way ANOVA with Dunnett's multiple comparisons.

Figure 2A:
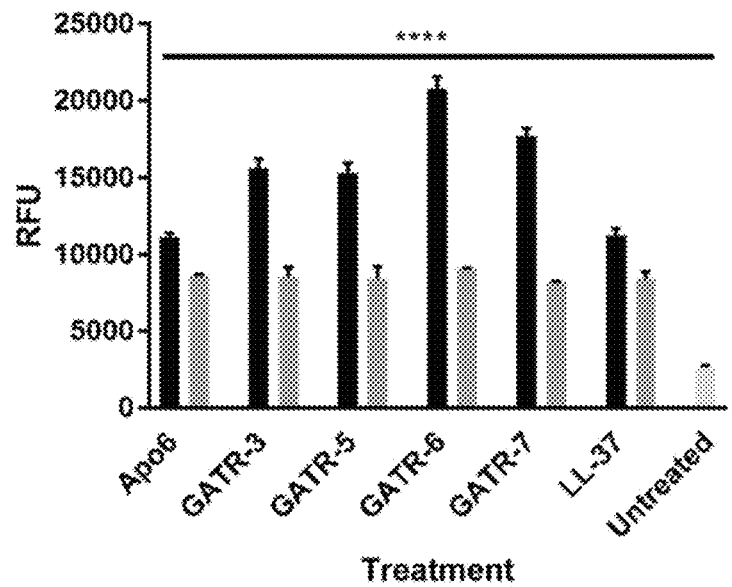
FIGS. 2A-2B are graphs showing GATR peptides disrupt the bacterial membrane of *F. tularensis* LVS.
Figure 2B:
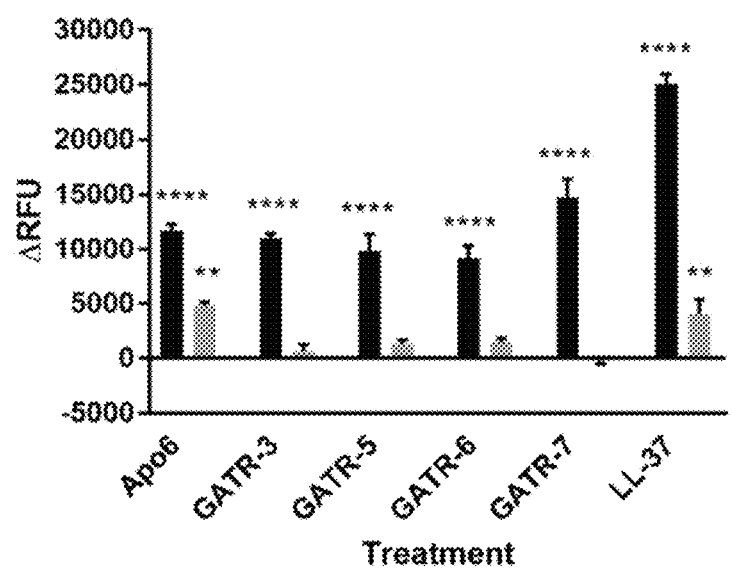

Ethidium bromide uptake assay. Pore formation in *F. tularensis* LVS cytoplasmic membrane was assessed using ethidium bromide as described previously with some modification. *F. tularensis* LVS was grown on chocolate II agar (48 h, 37° C., 5% $CO_2$) and colonies scraped into solution. Bacteria were suspended in 10 mM phosphate buffer to 0.5 McFarland standard. In a black polypropylene 96 well plate, 180 μL bacterial culture was then mixed with 10 μM ethidium bromide (final concentration) and incubated with varying concentrations of peptide. The plate was read in a Tecan infinite F200 fluorimeter every 2 min for 20 min at 37° C. (excitation=535 nm, emission=590 nm). Data shown in FIG. 2B is from the 20 min mark. Samples were run in triplicate on three separate occasions. Bacteria without peptide was used as a negative control, and LL-37 was used as positive control. Results were analyzed using a one-way ANOVA with Dunnett's multiple comparisons.

LPS binding. To examine the potential binding between *F. tularensis* LVS lipopolysaccharide and the GATR peptides, an LPS-binding assay using 1,9-dimethylmethyl blue (DMMB) was performed as previously described (Bland, J. M., et al., Mol Cell Biochem, 2001. 218(1-2): p. 105-11). *F. tularensis* subsp. *holarctica*, Strain LVS LPS was obtained from BEI Resources (NR-2627). Briefly, 150 μg/ml of LPS was incubated with 10 μg/ml of peptide in distilled endotoxin-free water for 1 h. The solution was added to DMMB, and the absorbance was read at 535 nm on a spectrometer. Samples were run in triplicate on two separate occasions. Results were analyzed using a one-way ANOVA with Dunnett's multiple comparisons.

Hemolysis assay. The hemolysis assay was performed using washed, defibrinated sheep blood as previously described (Barksdale, S. M., et al., Dev Comp Immunol, 2017). Sheep red blood cells (2% RBC) in phosphate buffered saline (PBS) were added to various dilutions of peptide reconstituted in PBS in a sterile U-bottom 96 well plate. The plate was incubated for 1 h at 37° C. and then centrifuged at 1000 rpm for 2 min. The supernatant was transferred to a fresh plate and read at 540 nm on a spectrometer. Sheep RBCs (2%) with PBS alone served as the negative control, and 2% RBC in water as the positive control. Experiment was performed twice in triplicate. A representative experiment is shown Results were analyzed using a one-way ANOVA with Dunnett's multiple comparisons.

Cytotoxicity assay. Cytotoxicity assays were performed using the Vybrant® MTT Cell Proliferation Assay Kit (Life Technologies) according to manufacturer's instructions. Assays were performed using human lung epithelial carcinoma line A549 (ATCC CCL-185) and human liver carcinoma line HepG2 (ATCC HB-8065), which were maintained at a low passage in Dulbecco s Minimal Essential Media (Life Technologies 11995073) with 10% heat-inactivated fetal bovine serum and 13 U/ml penicillin-streptomycin. 100 μg/ml of peptide was used for each experimental well, added to the cell growth medium, and incubated for 24 h. Each experiment was performed in triplicate two times. A representative experiment is shown. Results were analyzed using a one-way ANOVA with Dunnett's multiple comparisons.

Figure 4A:
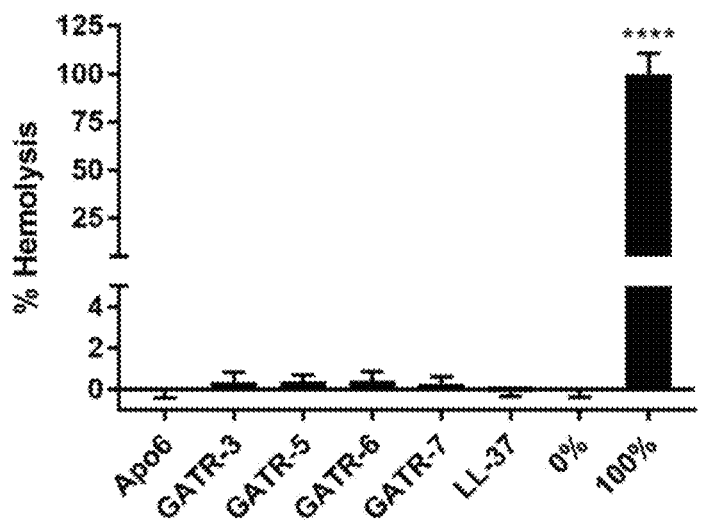
FIGS. 4A-4D relate to toxicity of GATR peptides.
Figure 4B:
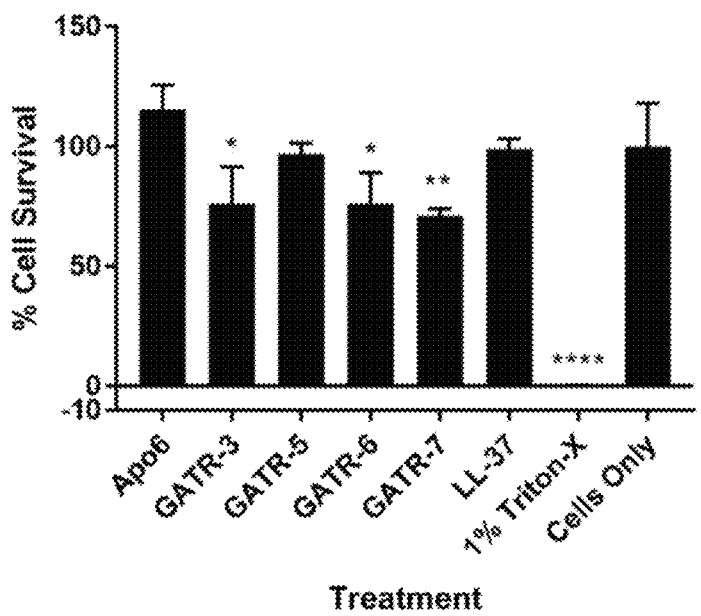
Figure 4C:
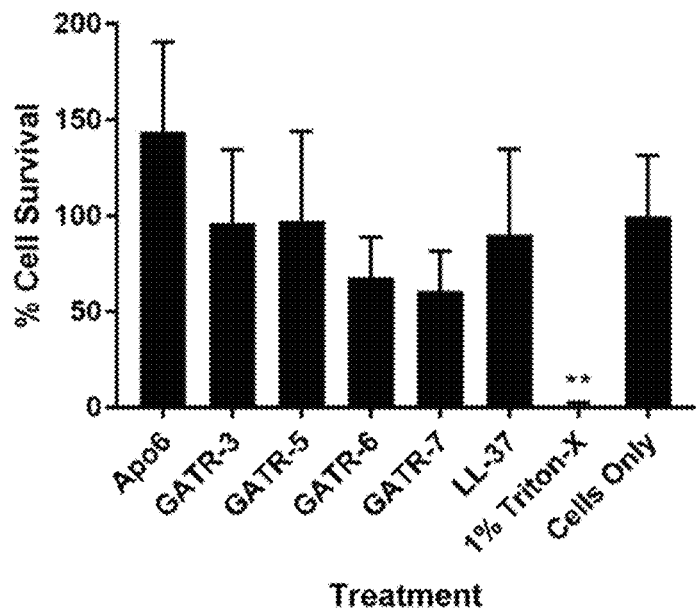
Figure 4D:
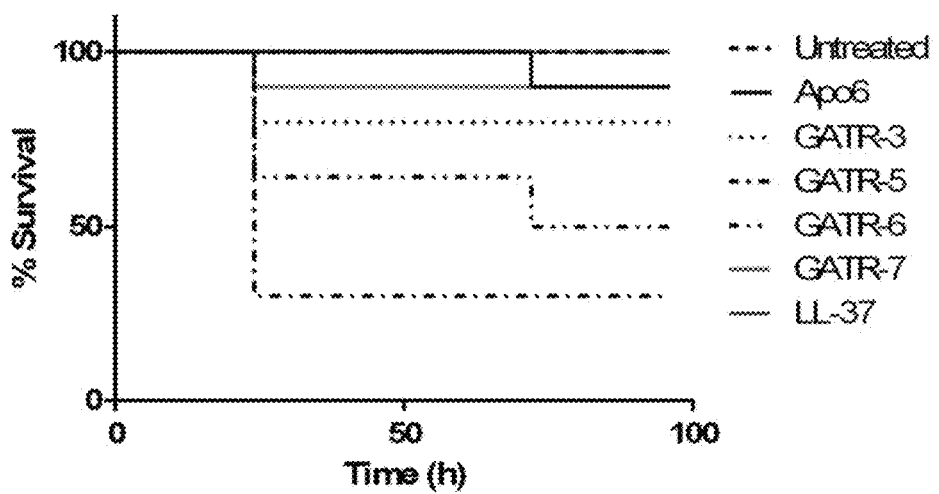

Peptide toxicity in *Galleria mellonella* larvae. Larvae were used to assess in vivo toxicity of peptides. *G. mellonella* larvae (wax moth larvae or "waxworms") were obtained from Vanderhorst Wholesale (Saint Marys, Ohio, USA). Ten larvae of equal size/weight were randomly assigned to each group and placed into labeled petri dishes. A 1 ml syringe with a 27 G needle was used to inject 10 μl containing 10 μg peptide into each larvae's right proleg. Survival was observed for 48 h. Results from one representative experiment of two total are shown in FIG. 4D and were analyzed using a Mantel-Cox test.

Figure 5:
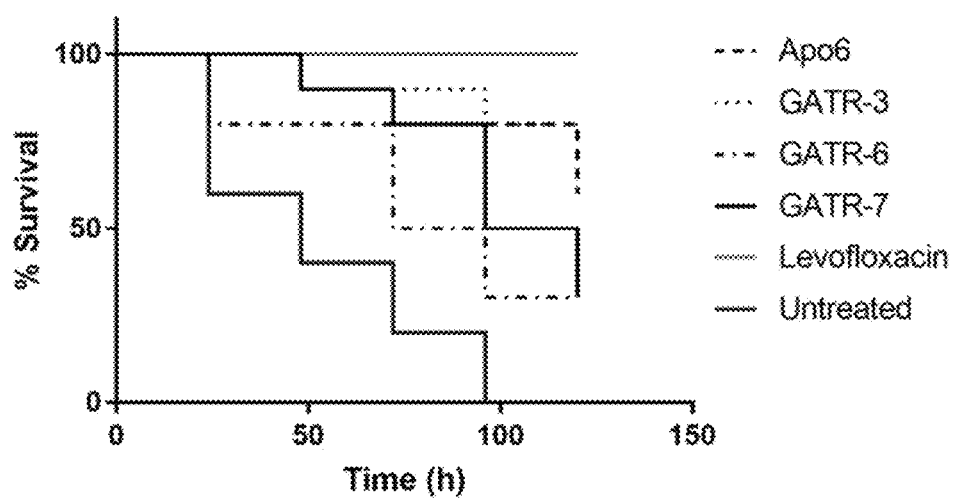
FIG. 5 shows *G. mellonella* survival following GATR peptide treatment. *G. mellonella* larvae were infected with *F. tularensis* LVS and treated with a single injection of 10 ng peptide or 10 µg levofloxacin (10 larvae/group). Survival was monitored for 120 h after infection.
Figure 6A:
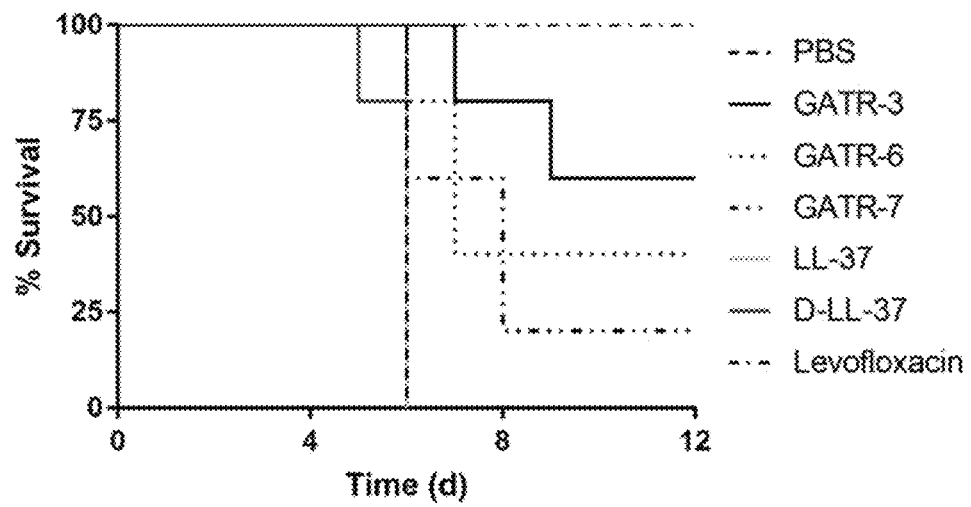
FIGS. 6A-6F relate to GATR peptide treatment of *F. tularensis* LVS infected mice. First, BALB/c mice were infected with 50 LD50 of *F. tularensis* LVS and treated with peptide 24 h before and 3, 24, and 48 h after infection (5 mice/group).
Figure 6B:
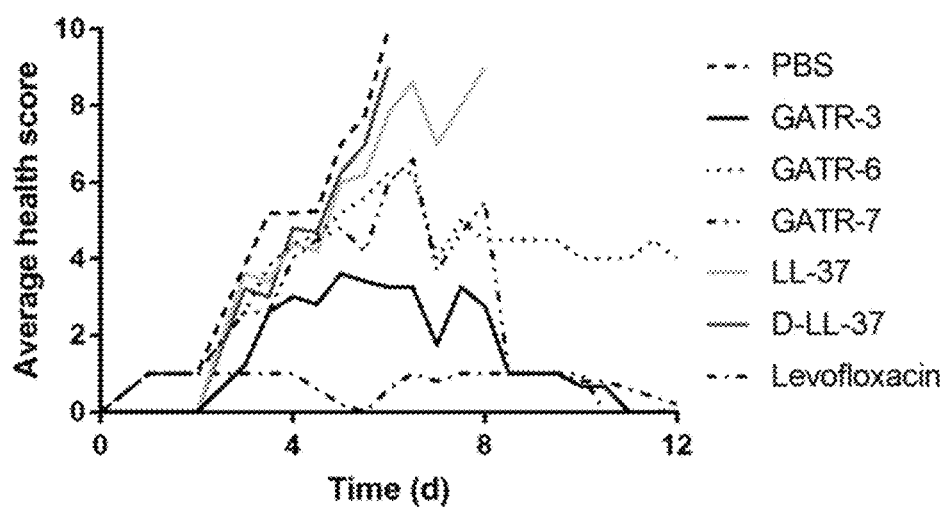
Figure 6C:
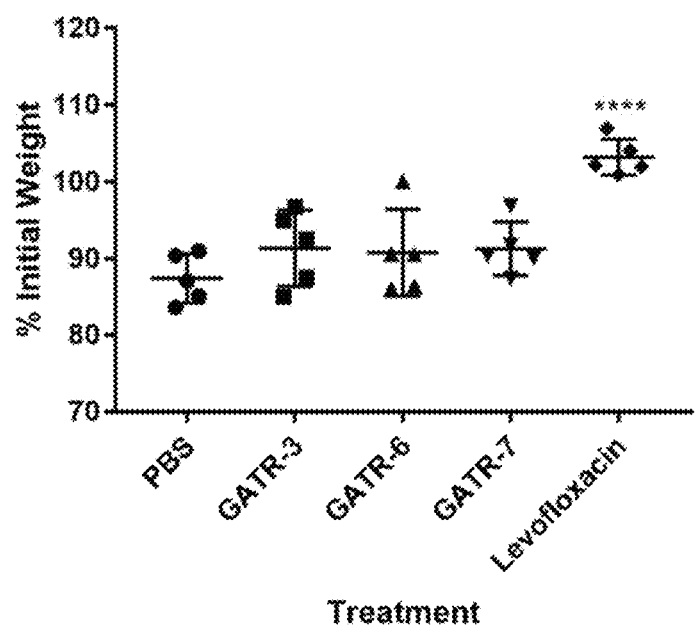
Figure 6D:
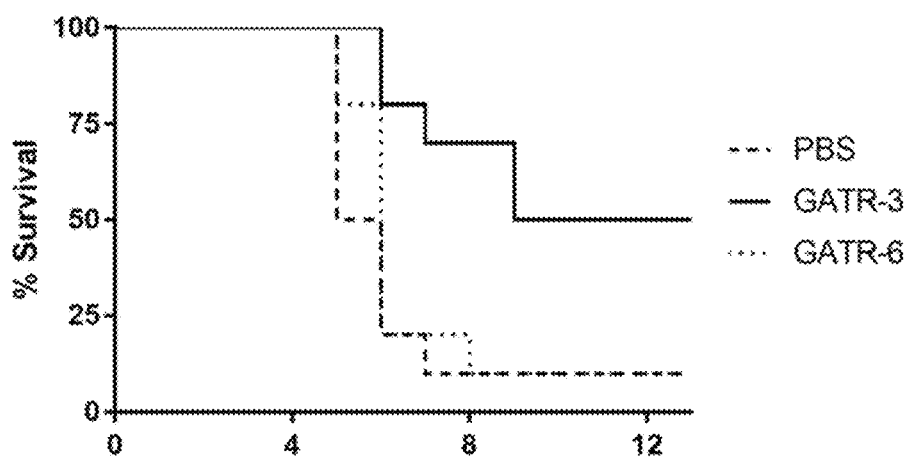
Figure 6E:
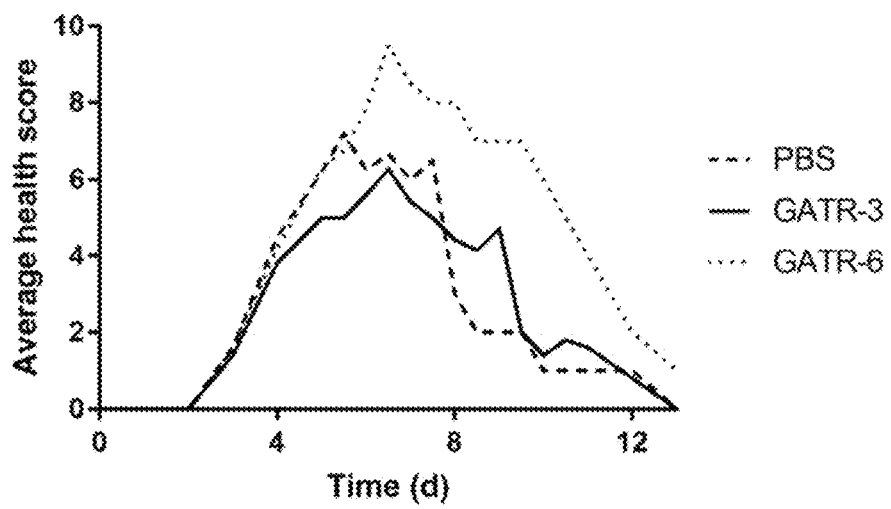
Figure 6F:
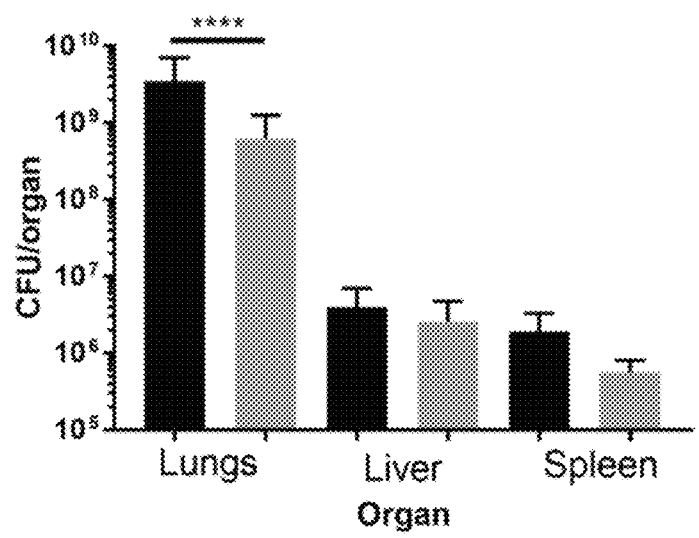
Figure 7A:
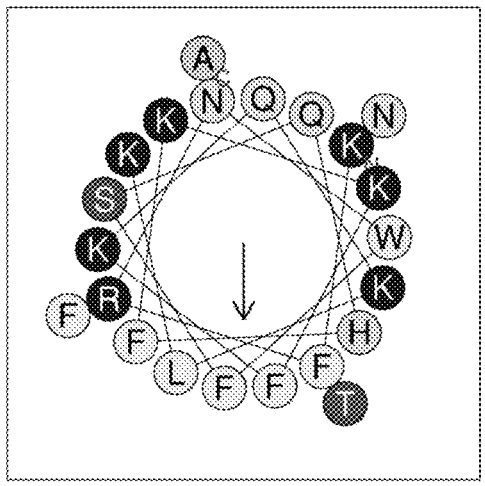
FIGS. 7A-7D shows helical wheels for GATR-3 (FIG. 7A), GATR-5 (FIG. 7B), GATR-6 (FIG. 7C) and GATR-7 (FIG. 7D) peptides.
Figure 7B:
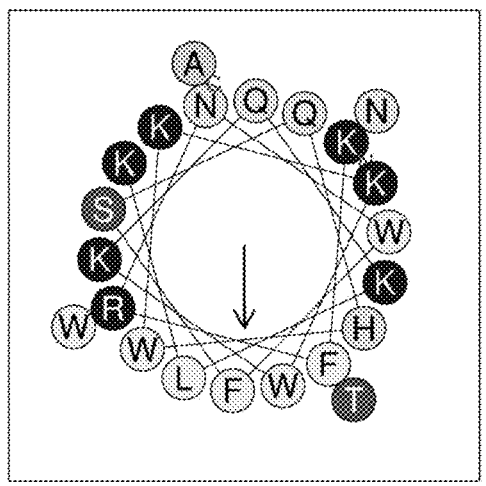
Figure 7C:
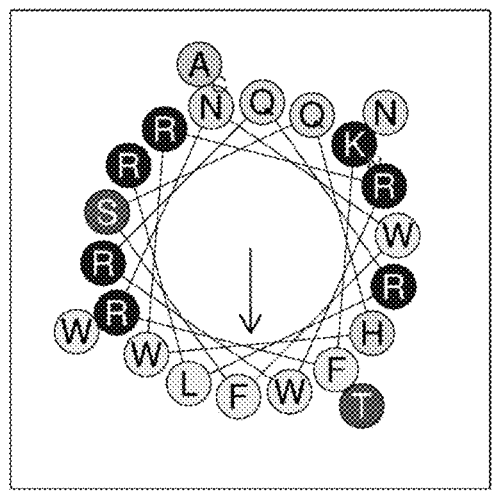
Figure 7D:
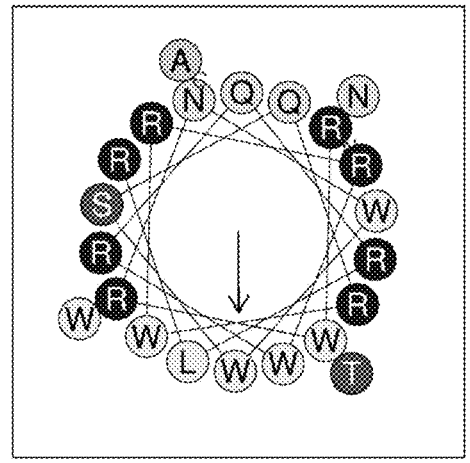

*G. mellonella* infection and treatment. Survival assay of wax moth larvae following *Francisella* infection with and without treatment was conducted as previously described (Propst, C. N., et al., Front Microbiol, 2016. 7: p. 696; Sprynski, N., et al., Methods Mol Biol, 2014. 1197: p. 3-9; Dean, S. N. and M. L. van Hoek, Virulence, 2015. 6(5): p. 487-503). *G. mellonella* (wax moth larvae or waxworms) were obtained from Vanderhorst Wholesale (Saint Marys, Ohio, USA). Ten larvae of equal size/weight were randomly assigned to each group and placed into labeled petri dishes. A 1 ml syringe with a 27 G needle was used to inject 10 μl of $1 \times 10^8$ CFU/ml of *F. tularensis* LVS into each larvae's right proleg. After a 60 min incubation to allow the infection to occur, the larvae were then injected with 10 ul of either PBS (no treatment) or 10 ng of the GATR peptides in the larvae's left proleg. Bacteria treated with 10 μg of levofloxacin was used as a positive control. The experiment was conducted twice; FIG. 5 shows one representative experiment.

Animal model of tularemia infection. Animal experiments were approved by and conducted in compliance with regulations of the Institutional Animal Care and Use Committee (Protocol #0328) of George Mason University (Fairfax, Va.). All experiments were carried out in accordance with the National Research Council's Guide for the Care and Use of Laboratory Animals (2011) and the Public Health Service Policy on Humane Care and Use of Laboratory Animals (2002). Female BALB/c mice 6-8 weeks of age were obtained from Jackson Laboratories. Animals were scored twice daily based on appearance, activity, respiration, and appearance following protocol. If mice were weighed, weights were taken individually prior to any experimental work each day.

For the inoculum, *F. tularensis* LVS was grown for 2 days on chocolate II agar (37° C., 5% CO2). Colonies were scraped and resuspended in sterile PBS to 0.5 McFarland Standard (which is equivalent to ~$10^7$ CFU/ml for this organism). 36 µl of this suspension was added to 10 ml of sterile PBS, and dilution plating was subsequently performed to confirm the inoculation dose. Mice were lightly anesthetized using isoflourane immediately before infection. Each mouse received an intranasal inoculation of 25 µl of this secondary suspension, evenly divided between both nares.

Peptide treatments were performed through intraperitoneal (IP) injections. Each injection consisted of 500 µl PBS containing 100 µg peptide or 60 µg levofloxacin. Treatments were performed 3 h, 24 h, and 48 h after infection. In addition, one group (5 mice) received a prophylactic treatment 24 h before infection, and one group received no treatment. Survival was tracked for 13 days. Survival results were analyzed using a Mantel-Cox test.

For organ burden studies, mice were infected and treated as above and sacrificed on Day 4. Lungs, livers, and spleens were harvested and homogenized in PBS using DT-20 tubes with an ULTRA-TURRAX Tube Drive (IKA, Wilmington, N.C., USA). Homogenate was plated on chocolate II agar and incubated for two days (37° C., 5% CO2). CFU counts were analyzed using a one-way ANOVA with Dunnett's multiple comparisons.

Statistical analysis. All statistical analysis was performed in GraphPad Prism 6.0 or 7.0. Tests performed are listed in each methods section and figure legend.

Example 2

Peptide Design and Properties

Apo6 is a naturally occurring (native) peptide identified intact from American alligator blood by de novo peptide mass-spectrometry sequencing (Bishop, B. M., et al., PLoS One, 2015. 10(2): p. e0117394; Juba, M. L., et al., J Proteome Res, 2015. 14(10): p. 4282-95). It is the C-terminal sequence of alligator apolipoprotein E and was discovered using BioProspector process (Bishop, B. M., et al., PLoS One, 2015. 10(2): p. e0117394). A series of GATR peptides, designated GATR-1 through GATR-7 (Table 1), were generated by introducing changes in the original Apo6 sequence, in order to improve the peptide's amphipathicity, hydrophobic face, or net charge, as described below.

GATR-1 was produced by replacing the native threonine (T) in position 2 with a phenylalanine (F) and substituting valine (V) at position 13 with phenylalanine (F). These changes increase the hydrophobic moment of the helical peptide from 0.484 µH to 0.564 µH as well as raising hydrophobicity from 0.085 H to 0.180 H.

GATR-2 was produced by replacing glutamic acid (E) at position 8 with glutamine (Q), glutamic acid (E) at position 15 with glutamine (Q), and aspartic acid (D) at position 19 with asparagine (N). These alterations to the sequence raise the peptides positive charge from +4 to +7 and hydrophobicity from 0.085 to 0.130. However, these changes also reduce the hydrophobic moment from 0.484 µH to 0.441 µH.

GATR-3 combines the T2/V13 and E8/E15/D19 amino acid substitutions of GATR-1 and GATR-2. These sequence modifications increase the overall peptide charge from +4 to +7, hydrophobic moment from 0.484 µH to 0.523 µH, and net hydrophobicity from 0.085 to 0.226.

GATR-4 was produced by adding NP to the N-terminus because N-capping peptides, particularly with a proline residue, has been reported to increase peptide stability and decrease protease susceptibility.

GATR-5 was produced by combining the GATR-2 alterations with substitutions of phenylalanine (F) at position 10 to tryptophan (W), valine at position 13 to tryptophan (W) and phenylalanine (F) at position 21 to tryptophan (W). These modifications increase the peptide charge from +4 to +7, the hydrophobic moment from 0.484 µH to 0.566 µH, and hydrophobicity from 0.085 H to 0.289 H.

In GATR-6, the sequence of GATR-5 was further modified by replacing the lysine (K) residues K11, K12, K14, K16, and K18 with arginine (R) residues. The physicochemical properties of GATR-6 are nearly identical to those of GATR-5. Both GATR-5 and GATR-6 have a net charge of +7, hydrophobic moments of 0.566 µH and 0.568 µH respectively, and hydrophobicities of 0.289 H and 0.284 H respectively.

GATR-7 was produced from the GATR-6 sequence by substituting the lysine (K) at position 1 with arginine (R), the phenylalanine (F) at position 2 to tryptophan (W), the phenylalanine (F) at position 6 to tryptophan (W) and the histidine (H) at position 9 to arginine (R). Due to these substitutions, GATR-7 is predicted to have a net charge of +8, which is higher than that of the other GATR peptides. Additionally, the hydrophobic moment of GATR-7 is 0.578 µH and its net hydrophobicity is calculated to be 0.273 H. These values are similar to those calculated for GATR-5 and GATR-6.

Example 3

GATR Peptides are Antibacterial Against *Francisella tularensis*

Apo6 has been shown to have activity against a broad range of pathogens in low salt buffer (Bishop, B. M., et al., PLoS One, 2015. 10(2): p. e0117394; Barksdale, S. M., et al., BMC Microbiol, 2016. 16(1): p. 189). Apo6 shares a salt-sensitive phenotype with LL-37 (Turner, J., et al., Antimicrob Agents Chemother, 1998. 42(9): p. 2206-14; Dean, S. N., et al., Natural and synthetic cathelicidin peptides with anti-microbial and anti-biofilm activity against *Staphylococcus aureus*. BMC Microbiol, 2011. 11: p. 114) and was found to be inactive in Muller-Hinton broth against these pathogens (Bishop, B. M., et al., PLoS One, 2015. 10(2): p. e0117394; Barksdale, S. M., et al., BMC Microbiol, 2016. 16(1): p. 189). Apo6 and the GATR peptides were first tested in MIC assays against *F. tularensis* LVS. Similar to its activity against other bacteria. Apo6 had no observable MIC against *F. tularensis* LVS at the concentrations tested. In addition, GATR-1, GATR-2, GATR-3, and GATR-4 were found to be inactive under these conditions; however, some inhibitory activity was observed when GATR-5, GATR-6, and GATR-7 are tested, with 85% inhibition at 41.5 µg/ml in the case of GATR-7 (FIG. 1). It appears that the antibacterial activity increases along with the hydrophobic moment.

Next, the antimicrobial activity of Apo6 and the GATR peptides were tested against *F. tularensis* LVS and *F. tularensis* NIH B38 strain in low salt buffer, which is an alternate measure of antimicrobial activity. $EC_{50}$ values are shown in Table 2.

TABLE 2

Antibacterial activity of GATR peptides against *F. tularensis* LVS and NIH B38[†]

| Peptide name | *F. tularensis* LVS | | *F. tularensis* NIH B38 | |
| --- | --- | --- | --- | --- |
| | $EC_{50}$ (95% CI) [μg/ml] | $EC_{50}$ [μM] | $EC_{50}$ (95% CI) [μg/ml] | $EC_{50}$ [μM] |
| Apo6 | 6.8 (5.9-7.8) | 2.5 | 16 (8.6-31) | 5.89 |
| GATR-1 | 0.76 (0.54-1.1) | 0.26 | 16 (9.5-27) | 5.62 |
| GATR-2 | 2.4 (1.5-3.7) | 0.86 | 11 (7.7-15) | 3.9 |
| GATR-3 | 0.53 (0.42-0.66) | 0.19 | 0.80 (0.56-1.1) | 0.28 |
| GATR-4 | 11.0 (7.5-16) | 3.7 | Not active | Not active |
| GATR-5 | 0.76 (0.56-1.0) | 0.26 | 1.9 (1.6-2.3) | 0.65 |
| GATR-6 | 0.89 (0.60-1.3) | 0.29 | 0.16 (0.06-0.43) | 0.051 |
| GATR-7 | 1.0 (0.81-1.3) | 0.32 | 1.7 (1.4-2.1) | 0.53 |
| LL-37 | 0.21 (0.14-0.31) | 0.047 | 0.13 (0.076-0.21) | 0.028 |

[†]$EC_{50}$ values were determined in Buffer Q against *F. tularensis* LVS and *F. tularensis* NIH B38 (the Type strain). For statistical comparison, the 95% confidence intervals (p < 0.05) are listed. The values are also expressed as μM for direct comparison.

These experiments were performed using LL-37 as a positive control, which was found to be extremely effective against *F. tularensis* ($EC_{50}$=0.209 μg/ml), similar to the $EC_{50}$ reported for *F. novicida*. As shown in Table 2, it was found that the ECso values of the GATR peptides were generally lower than that of Apo6 (6.82 μg/ml vs *F. tularensis* LVS; 16.3 μg/ml vs. *F. tularensis* NIH B38), with the exception of GATR-4, which had a similar $EC_{50}$ against *F. tularensis* LVS (11.0 μg/ml) but was not effective at concentrations tested against *F. tularensis* NIH B38. Four peptides (GATR-3, GATR-5, GATR-6, and GATR-7) had $EC_{50}$ values lower than 2 μg/ml against both strains of *F. tularensis*, and thus were selected as the most effective peptides against *Francisella*. For comparison, the $EC_{50}$ of levofloxacin for *F. tularensis* subsp. LVS is 0.00827 μg/ml (8.27 ng/ml) (Dean, S. N., et al., Front Microbiol, 2011. 2: p. 128).

Apo6, the most effective GATR peptides, and LL-37 were then tested against the highly virulent strain *F. tularensis tularensis* SchuS4 in MIC and low salt assays. Results are shown in Table 3.

TABLE 3

Antibacterial activity of selected GATR peptides against *F. tularensis tularensis* SchuS4[††]

| Peptide Name | MIC [μg/ml] | $EC_{50}$ (95% CI) [μg/ml] | $EC_{50}$ [μM] |
| --- | --- | --- | --- |
| Apo6 | Not tested | Not active | Not active |
| GATR-3 | >83.3 | 28.6 (13.3 to 61.6) | 10.0 |
| GATR-6 | >83.3 | 32.3 (15.8 to 66.2) | 10.4 |
| GATR-7 | 41.7 | 24.2 (wide) | 7.47 |
| LL-37 | Not tested | 0.562 (0.195 to 1.61) | 0.125 |

[††]The more active GATR peptides were tested against *F. tularensis* SchuS4 in CAMHB with 2% IsovitaleX and in Buffer Q. For statistical comparison, the 95% confidence intervals (p < 0.05) are listed. The $EC_{50}$ values are also expressed as μM for direct comparison.

Though Apo6 is not effective against *F. tularensis* SchuS4, GATR-3, GATR-6, and GATR-7 are each moderately effective against this strain, with $EC_{50}$ values around 30 μg/ml. Interestingly, though these peptides are not particularly effective against less virulent strains of *F. tularensis* in MIC assays, GATR-7 displays comparatively strong activity with a MIC of 41.7 μg/ml.

*Francisella* is highly resistant to cationic cyclic peptide antibiotics such as polymyxin B. Indeed, *Francisella* selective growth media contains 100 mg/ml polymyxin B (Petersen, J. M., et al., Lett Appl Microbiol, 2009. 48(6): p. 663-7). The resistance to polymyxin B is thought to be due to the special structure of the lipopolysaccharide (LPS) of *Francisella* (Gunn, J. S. and R. K. Ernst, Ann N Y Acad Sci, 2007. 1105: p. 202-18; Kanistanon, D., et al., Infect Immun, 2012. 80(3): p. 943-51). Thus, *Francisella* is considered to be resistant to this class of cyclic peptide antibiotics, which are sometimes called cationic antimicrobial peptides by other researchers. Experiments to introduce such antimicrobial peptides in the lung by Flick-Smith et al. only modestly increased the time-to-death of mice infected with *F. tularensis* LVS (Flick-Smith, H. C., et al., Peptides, 2013. 43: p. 96-101).

Previously, C-terminal fragments of apolipoprotein C-1 from *Alligator mississippiensis* have been identified. These helical fragments, called Apo5 and Apo6, were found to have broad-spectrum activity against a variety of pathogens, including *Pseudomonas aeruginosa*, *Staphylococcus aureus*, and *Acinetobacter baumannii* (Bishop, B. M., et al., PLoS One, 2015. 10(2): p. e0117394; Barksdale, S. M., et al., BMC Microbiol, 2016. 16(1): p. 189). In general, these peptides had strong anti-*Francisella* activity in low-salt buffer, with several peptides exhibiting $EC_{50}$ values under 3 μg/ml. When these peptides were tested against *F. tularensis* subspecies, it was found that Apo5 and Apo6 were generally less effective against these subspecies than against other Gram-negative bacteria tested, with $EC_{50}$ values ranging from low (~6 μg/ml) against *F. tularensis* LVS to much higher (~16 μg/ml) against *F. tularensis* NIH B38.

The GATR peptides (GATR-1 to -7) were designed based on changes to the peptide sequences. Individually, these modifications were anticipated to minimally impact the peptide structural properties and preserve amino acid side-chain groups present in the parent peptide that may participate in critical interactions with bacterial targets such as the membrane or LPS. By substituting amino acids to increase peptide hydrophobicity and overall positive charge, peptides with stronger in vitro and/or in vivo activity were surprisingly discovered. All of the peptides, except GATR-4, exhibited superior performance over the parent peptide Apo6 against *F. tularensis* LVS under EC50 conditions. All the GATR peptides, except GATR-1 and GATR-2, also demonstrated superior performance against *F. tularensis* NIH B38, the *F. tularensis* type strain, compared to parent peptide Apo6. The more substituted peptides, GATR-5, -6, and -7, began to show activity in cation-adjusted Mueller Hinton Broth, though a MIC could not be determined based upon the concentrations tested. The most efficacious peptides were also found to have stronger activity against *F. tularensis* SchuS4 compared to Apo6. Most notably, GATR-7 had a determinable MIC at concentrations tested.

Example 4

GATR Peptides Interact with the Cytoplasmic Membrane of *F. tularensis* LVS

Without wishing to be bound by any particular theory, it is believed that as part of their mechanism of action, antimicrobial peptides can cause bacterial membrane disruption, ranging from slow leakage of cellular contents owing to membrane thinning to formation of large monomeric pores that can lead to cell death (Travis, S. M., et al., Infection and Immunity, 2000. 68(5): p. 2748-2755). In order to evaluate the interaction between the peptides and the bacterial cytoplasmic membrane, two fluorescence-based studies were conducted.

One of the ways in which the structural integrity of cell membrane can be compromised is through disruption of membrane potential. The depolarization of bacterial membranes was assessed using $DiSC_3(5)$, a membrane potential sensitive dye, which intercalates itself in the lipid bilayer resulting in the self-quenching of the dye. If depolarizing compounds are added, the potential decreases, and $DiSC_3(5)$ is released into the solution causing an increase in fluorescence relative to the reduction of membrane potential. FIG. 2A indicates a concentration-dependent increase in fluorescence when F. tularensis LVS was treated with two different concentrations of peptides (10 μg/ml and 1 μg/ml). Apo6 and the GATR peptides dissipated the membrane potential in F. tularensis LVS at 1 μg/ml, indicating that depolarization of cytoplasmic membrane is a primary mechanism of action of Apo6 and GATR peptides. In addition, the GATR peptides were much more effective in disrupting the membrane potential at 10 μg/ml compared to the parent peptide Apo6 (p values<0.0001).

Greater disruption can lead to the formation of larger, less transient holes or pores in the bacterial membrane, which will lead to bacterial death. To examine this effect, a membrane disruption assay was conducted using ethidium bromide (EtBr). This larger molecule will pass through a damaged membrane and intercalate with the bacterial DNA resulting in increased fluorescence proportional to the level of membrane disruption. We observed that F. tularensis LVS was sensitive to pore-formation by Apo6 and GATR peptides (FIG. 2B), evidenced by a significant RFU difference between the control and treated bacteria (p-values<0.05). At 10 μg/ml, all peptides except GATR-7 demonstrate a significant change in RFU, indicating pore-formation by most of these peptides. Apo6 and GATR-5 also display significant pore formation at a lower concentration of 1 μg/ml. However, GATR-3, GATR-6, and GATR-7 do not show significant pore formation compared to the untreated bacteria at 1 μg/ml. LL-37 was used as positive control in the depolarization and pore formation studies of the peptides.

Previous studies showed that the Apo6 peptide affected bacteria by disrupting the bacterial membrane, primarily through depolarization (Barksdale, S. M., et al., BMC Microbiol, 2016. 16(1): p. 189). To examine if this was also the case with the synthetic peptides with F. tularensis, membrane binding and disruption were examined. $DiSC_3(5)$ measures depolarization and transient holes in a previously hyperpolarized membrane. It was found that as hydrophobicity and cationicity increase, so does depolarization activity. However, this is not the case when the ethidium bromide uptake assay was performed, which measures larger pores or disruption that allow the passage of ethidium bromide into the cell. While Apo6 shows significant membrane disruption at both 10 and 1 μg/ml tested, none of the other peptides show significant depolarization at 1 μg/ml. In general, the GATR peptides have a similar ΔRFU to Apo6 at 10 μg/ml. It is not clear why this occurs based on physico-chemical properties. The charge and hydrophobicity of Apo6 is much lower than that of the GATR peptides but considering the greater antimicrobial efficacy of the GATR peptides, it appears that the pore-forming activity is less important to its antibacterial mechanism than the depolarization activity, which may suggest an intracellular target.

Example 5

GATR Peptides Bind F. tularensis LVS Lipopolysaccharide (LPS)

Figure 3:
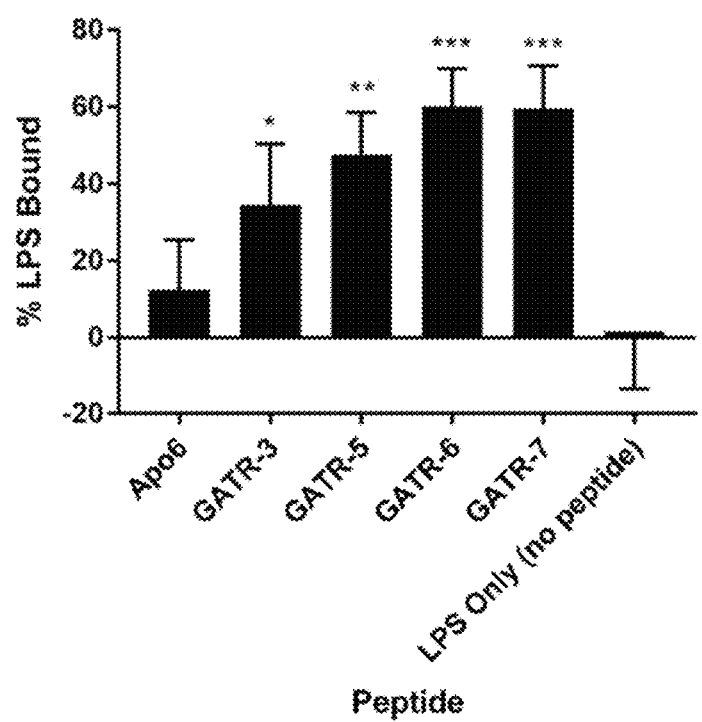
FIG. 3 is a graph showing GATR peptides bind *F. tularensis* LVS LPS. 150 µg/ml of LPS was incubated with 10 µg/ml of peptide in distilled endotoxin-free water for 1 h and then added to DMMB. The experiment was performed twice with 3 replicates per experiment. Results were analyzed using a 1 way ANOVA with Dunnett's multiple comparisons tests. (* $p<0.05$;  $p<0.01$; * $p<0.001$). Error bars indicate standard deviation.

To test binding between GATR peptides and LPS, a dimethylmethylene blue (DMB) dye LPS-binding assay was employed. The positively charged dye competes with the positively charged peptide to bind to the negatively charged moieties on the LPS. Upon binding, the dye changes color from blue to purple/pink. As shown in FIG. 3, although the parent peptide Apo6 does not significantly bind F. tularensis LVS LPS, the GATR peptides tested significantly bind this LPS (p value<0.05), however, Apo6 does not significantly bind the LVS LPS. GATR peptides with greater charge and hydrophobicity (GATR-6 and GATR-7) bind this LPS in greater amounts than do less charged and hydrophobic peptides (GATR-3 and GATR-5). Thus, LPS binding might contribute to the anti-Francisella activity of the GATR peptides.

Some antimicrobial peptides, such as LL-37, bind to bacterial LPS. In addition, some apolipoproteins have been shown to bind LPS. Prior experiments had shown that Apo6 did not bind E. coli LPS (data not shown), and it was found, similarly, that Apo6 does not significantly bind F. tularensis LVS LPS. The GATR peptides, however, were found to bind greater amounts of F. tularensis LVS LPS as hydrophobicity and cationicity increased, leveling off with GATR-6 and GATR-7. It is unclear if increasing LPS binding leads to increased depolarization, but it is possible that increased attraction between peptide and LPS allows higher-binding peptides to better associate with the membrane. It seems that there is no correlation, positive or negative, between LPS binding and pore formation in the membrane.

Example 6

Toxicity of the GATR Peptides

To examine whether the GATR peptides may be toxic to mammalian cells (particularly those peptides with higher charge), hemolysis assays, cytotoxicity assays using the MTT assay, and toxicity experiments in G. mellonella waxworms were performed.

First, hemolysis assays using sheep red blood cells were performed at peptide concentrations of 100 μg/ml for 1 h. All peptides showed negligible hemolysis averaging less than 0.5%, indicating no hemolytic properties (FIG. 4A).

Next, cytotoxicity of the GATR peptides were measured by using the MTT assay as a measure of cell viability following peptide treatment. A549 human lung epithelial cells and HepG2 liver cells were treated with 100 μg/ml peptide for 24 h. Shown in FIGS. 4B and 4C, some statistically significant suppression of cell proliferation was seen in A549 cells for GATR-3, GATR-6, and GATR-7; however, no peptides show statistical suppression of cell growth when tested against HepG2 cells.

Toxicity assays were also performed in the G. mellonella waxworm model. In groups of 10, each larva received 10 μg of peptide, and survival was assessed for 48 h. After this time period, waxworms treated with GATR-3, GATR-6, and GATR-7 were not found to have significant death as measured by larvae survival (FIG. 4D). However, GATR-5 treated waxworms had only 30% survival, indicating that this peptide could potentially be toxic in an animal model (p=0.0014). Further testing in mice will be done to assess the potential toxicity of these peptides.

Example 7

Waxworm In Vivo Infection Survival Assay

Analysis of the efficacy of antimicrobials utilizing in vivo models is conducted prior to clinical trials. Ideally a mammalian animal model should be employed in order to test the in vivo capabilities of antimicrobials; however, alternative models may be appropriate for screening of lead antimicrobial candidates ($EC_{50}$ activity ≤10 µg/ml). *Galleria mellonella*, the greater wax moth, has been proposed as an alternative model that is relatively easy to obtain and has a system of antimicrobial protection similar to that of mammals. These factors make larvae of *G. mellonella* a good model of infection for various pathogenic microorganisms (Propst, C. N., et al., Front Microbiol, 2016. 7: p. 696; Sprynski, N., et al., Methods Mol Biol, 2014. 1197: p. 3-9; Aperis, G., et al., Microbes Infect, 2007. 9(6): p. 729-34; Blower, R. J., et al., Virulence, 2017: p. 1-7). *G. mellonella* has been previously used as an infection model for in vivo effect of antimicrobial peptides and antibiotics against *Francisella* spp. Infections (Propst, C. N., et al., Front Microbiol, 2016. 7: p. 6%; Aperis, G., et al., Microbes Infect, 2007. 9(6): p. 729-34).

To evaluate the ability of selected antimicrobial peptides to prolong survival of infected *G. mellonella*, larvae were infected with *F. tularensis* LVS and then treated with a single dose of 10 ng of peptides. Shown in FIG. 5, *G. mellonella* showed statistically significant improved survival when compared to untreated groups ($p<0.05$) when treated with Apo6 and GATR peptides, with GATR-3 having the strongest effect (80% survival, $p=0.0001$). The parent peptide, Apo6, was the next best candidate (60% survival, $p=0.0002$). While GATR-5-treated *G. mellonella* initially demonstrated a strong prolonged survival rate, all of the larvae succumbed to infection by 120 h (0% survival, $p=0.0008$). GATR-6—(30% survival, $p=0.045$) and GATR-7—(30% survival p value=0.0015) treated waxworms also showed significant prolonged survival.

Example 8

Murine Model In Vivo

Apo6, GATR-3, GATR-6, and GATR-7 were tested in a murine model of pulmonary tularemia. In addition, LL-37 and D-LL-37 were tested in this model. LL-37 had stronger activity in vitro than any of the GATR peptides. Previously, Flick-Smith et al. evaluated the use of LL-37 as a post-exposure intranasal therapy in the treatment of pulmonary tularemia by delivering the peptide directly to the lungs (Flick-Smith, H. C., et al., Peptides, 2013. 43: p. 96-101). In that report, LL-37 extended mean time till death but did not increase survival in treated animals.

In this study, systemic peptide delivery via the intraperitoneal (IP) route of treatment appears to have no adverse effect on survival in response to this peptide, i.e. the peptide was not toxic when delivered systemically.

Previously, it was found that D-LL-37 has increased activity antimicrobial and protease resistance (Dean, S. N., et al., BMC Microbiol, 2011. 11: p. 114; Dean, S. N., et al., Front Microbiol, 2011. 2: p. 128), making it an attractive peptide to use in vivo. However, D-LL-37 had similar activity in this animal model to LL-37 in that it did not extend survival or rescue mice, nor did these peptides lessen signs of disease. Survival data and health scores are shown in FIGS. 6A and 7B.

In the first set of experiments, mice (5/group) were given 1 prophylactic peptide treatment 1 day before infection (Day −1) and 3 treatments after infection at 3, 24, and 48 h. Each intra-peritoneal (IP) injection delivered 5 mg/kg of peptide. Survival is shown in FIG. 6A. In this model, GATR-3 was found to be the most successful peptide, with 60% survival ($p=0.0047$) compared to the PBS-injected control, which had a mean time till death (MTD) of 6 days and 0% survival. GATR-6 saved 40% of mice ($p=0.0237$) compared to the control. GATR-7 saved 20% of mice, but Mantel-Cox tests indicate this was not significant ($p=0.0736$). When average health scores are examined in FIG. 6B, GATR-3 delays the time of disease onset from day 1 to day 3 and lessens severity of signs over the course of infection. GATR-6 and GATR-7 do not delay disease onset, but severity of signs are slightly lessened compared to the untreated control. For this set of experiments, mice were weighed daily in the morning. Weights from day 4 are compared in FIG. 6C. None of the GATR peptide treated mice show a significant difference in weight change compared to the untreated control.

In the second set of experiments, the prophylactic pretreatment was not given, and larger groups were used (10 mice/group). Mice received only the 3 treatments after infection at 3, 24, and 48 h. Because LL-37, D-LL-37, and GATR-7 were not found to significantly rescue mice in the first set of studies, they were not used in these experiments. Only GATR-3 and GATR-6 were tested. In the survival study shown in FIG. 6D, GATR-3 once again was the most successful peptide, with 50% survival ($p=0.0053$) compared to the untreated control, which had 10% survival and a mean time till death of 5.5 days. However, GATR-6 was not found to have significant survival in this study (10% survival, $p=0.4347$), though mean time till death (MTD) was extended to 6 days. This may indicate the prophylactic treatment was important for the efficacy of GATR-6. When average health scores were compared in FIG. 6E, differences between peptide-treated and untreated groups were not as apparent as in FIG. 6B. All groups had signs of disease onset on day 3. Disease signs of GATR-3-treated mice were only slightly lessened compared to the untreated group, while signs of GATR-6-treated mice were slightly more severe than the untreated mice.

Because GATR-3 rescued mice in both sets of experiments, an organ burden study was performed with this peptide on day 4 to determine the bacterial burden in the lungs, spleen, and liver (3 mice/group), as shown in FIG. 6F. Though no significant difference was found between the bacterial burden in the spleens and livers of GATR-3-treated and untreated mice, the bacterial numbers were found to be significantly lower in lungs ($p<0.0001$). Thus, the survival benefit may have been due to reduced lung burden as opposed to overall bacterial clearance.

The best performing peptides, GATR-3, GATR-6, and GATR-7, were tested for activity in vivo. Though GATR-7 had the best performance in MIC assays, initial studies in *G. mellonella* larvae did not clearly show this peptide to be the best performer. Instead, GATR-3 and then the parent peptide Apo6 saved more larvae from a lethal *F. tularensis* infection, though GATR-6 and GATR-7 also significantly rescued these insects. Because the in vitro and in vivo data together did not point to a clear front-runner peptide, the three top-performing peptides (GATR-3, GATR-6, GATR-7) were tested in a murine model infected with pulmonary tularemia. In initial studies, Apo6 was tested in vivo because of its strong performance in *G. mellonella* studies. However, this peptide was not reliably effective in murine studies (data not shown). In a set of further experiments, GATR-3, GATR-6, and GATR-7, as well as LL-37 and its D-enantiomer D-LL-37 were tested. It was previously shown that LL-37 is a highly effective peptide against *Francisella* in vitro. This peptide is the only other peptide that has been tested in a murine pulmonary tularemia model. Flick-Smith et al. previously reported that when LVS-infected mice are treated with LL-37 via the intranasal route, the peptide significantly extended mean time to death, but did not ultimately rescue any mice. The present experiment treated at a higher concentration than Flick-Smith et al. via IP, and similarly found that LL-37 had no effect on survival of infected mice. D-LL-37 was also tested in vivo because this chiral enantiomer is equally or more effective than the native peptide (Dean, S. N., et al., BMC Microbiol, 2011. 11: p. 114; Dean, S. N., et al., Front Microbiol, 2011. 2: p. 128). In addition, it has the advantage of protease resistance, which should allow it to circulate in the body longer. When D-LL-37 was tested in this model, this peptide was also ineffective at rescuing infected mice or even prolonging mean time till death. Thus, LL-37 is not effective against a pulmonary-based infection when given systemically, in agreement with previous reports.

When the GATR peptides were tested in this model with a prophylactic treatment, it was found that both GATR-3 and GATR-6 significantly rescued mice infected with *F. tularensis* LVS. GATR-7 did not, though this peptide had the strongest activity in MIC assays, which are considered the gold standard for activity. In a second set of experiments, GATR-3 and GATR-6 were tested in larger groups without the prophylactic treatment. GATR-3 maintained its efficacy without the prophylactic treatment, while GATR-6 did not. This indicates that the pre-infection administration is important for the activity of GATR-6.

Other groups have used peptides to treat a variety of bacterial infections in animal models with varying levels of success. Silva et al. treated mice infected with *E. coli* and *S. aureus* with peptides derived the marine tunicate *Styela clava* and found that a single dose of 10 mg/kg yielded survival rates of 80-90% (Silva, O. N., et al., Sci Rep, 2016. 6: p. 35465). In another study, it was found that a single 80-200 mg/kg dose boosted survival of rainbow trout infected with *Yersinia ruckeri* from 20% to 70% (Chettri, J. K., et al., J Fish Dis, 2016). Additionally, mice infected with *Bacillus anthracia* spores were treated with a single dose of 1 mg/kg synthetic protease-resistant peptides, and survival was boosted to 20-30% (Teyssieres, E., et al., J Med Chem, 2016. 59(18): p. 8221-32). Thus, 3-4 doses of 5 mg/kg GATR-3 yielding 50-60% survival in infected mice compares favorably with the results of other trials. The dosage of GATR-3 in this study is also comparable to levofloxacin (5 mg/kg vs. 3 mg/kg), though GATR-3 did not rescue all mice in the treated cohort. Larger doses of GATR-3 may increase efficacy of the peptide. Based on the treatment used in the study, a preliminary dosage for human infection can be inferred using guidelines put forth by the FDA (Guidance for Industry: Estimating the Maximum Safe Starting Dose in Initial Clinical Trials for Therapeutics in Adult Healthy Volunteers F.a.D. Administration, Editor. 2005: Rockville, Md.). The dosage of 5 mg/kg in mice would convert to approximately 0.4 mg/kg in humans with a dose of 24 mg presuming a 60 kg human. Clinically, tularemia is treated with 400 mg of intravenous ciprofloxacin twice per day for 10 days or 500-750 mg oral ciprofloxacin twice per day for at least 14 days (Generali, J. A. and D. J. Cada, Hosp Pharm, 2015. 50(4): p. 274-6). It is likely that a successful clinical course of treatment using GATR-3 would not require as large a dose as recommended for ciprofloxacin.

*F. tularensis* disseminates from the lung to the liver and spleen during infection. GATR-3 was tested in an organ burden study to examine whether bacterial burden reduction was the cause for in vivo activity. Though bacterial burden was reduced in the lungs of GATR-3-treated mice, it was not reduced in the liver or spleen.

We claim:

1. A peptide comprising the amino acid sequence set forth in SEQ ID NO:2, 4, 5, 6, 7, or 8.

2. A composition comprising the peptide of claim 1.

3. The composition of claim 2 further comprising an excipient.

4. An article of manufacture comprising the peptide of claim 1.

5. A kit comprising the peptide of claim 1.

6. A method for treating infection by a microbial organism in a subject, the method comprising administering to the subject the peptide of claim 1.

7. The method of claim 6, wherein about 0.01 µg to about 100 g per kg of body weight of the peptide is administered to the subject.

8. The method of claim 6 further comprising reducing biofilm levels or inhibiting biofilm formation in the subject prior to the administering.

9. The method of claim 8, wherein reducing biofilm levels or inhibiting biofilm formation comprises providing the peptide to the subject (i) in a sub-anti-microbial amount that is sub-anti-microbial but is effective to reduce biofilm levels or inhibit biofilm formation, or (ii) under a condition that is sub-anti-microbial but is effective to reduce biofilm levels or inhibit biofilm formation.

10. The method of claim 9, wherein the sub-anti-microbial condition is a high salt condition.

11. A method for preventing, reducing or inhibiting growth of a microbiol organism or biofilm on a surface, the method comprising contacting the surface with a composition comprising the peptide of claim 1.

12. A method for promoting wound healing in a subject, the method comprising administering to the subject the peptide of claim 1.

13. A method for treating or preventing endotoxemia in a subject, the method comprising administering to the subject an amount of the peptide of claim 1 effective to treat or prevent endotoxemia in the subject.

14. The method of claim 13, wherein the endotoxemia comprises microbial organism-induced inflammation.

15. A method for determining lipopolysaccharide (LPS) in a sample, the method comprising contacting the sample with the peptide of claim 1 under a condition such that the LPS binds to the peptide to form a complex; and detecting the complex.

16. A method for diagnosing an LPS-associated disorder in a subject, the method comprising forming a complex between LPS and the peptide of claim 1 under a condition such that the LPS binds to the peptide to form the complex; and detecting the complex.

17. A method for treating a composition comprising LPS, the method comprising contacting the composition with the peptide of claim 1 under a condition such that the LPS binds to the peptide to form a complex; and separating the complex from the composition, thereby reducing or eliminating the LPS from the composition.

* * * * *